United States Patent
Cartwright et al.

(10) Patent No.: US 11,786,621 B2
(45) Date of Patent: Oct. 17, 2023

(54) REUSABLE TORTUOUS PATH FILTERS FOR STERILIZATION CONTAINERS

(71) Applicant: CareFusion 2200, Inc., San Diego, CA (US)

(72) Inventors: Jason Cartwright, Libertyville, IL (US); Brandon Toth, Vernon Hills, IL (US); Benjamin Hopwood, Towson, MD (US); Bradley Thomas Williams, Mundelein, IL (US); Andrew VanDeWeghe, Grayslake, IL (US); Atif Yardimci, Chicago, IL (US)

(73) Assignee: CareFusion 2200, Inc., San Diego, CA (US)

( * ) Notice: Subject to any disclaimer, the term of this patent is extended or adjusted under 35 U.S.C. 154(b) by 331 days.

(21) Appl. No.: 17/066,628

(22) Filed: Oct. 9, 2020

(65) Prior Publication Data

US 2021/0106709 A1    Apr. 15, 2021

Related U.S. Application Data

(60) Provisional application No. 62/913,446, filed on Oct. 10, 2019.

(51) Int. Cl.
 *A61L 2/26* (2006.01)
(52) U.S. Cl.
 CPC ........... *A61L 2/26* (2013.01); *A61L 2202/182* (2013.01)
(58) Field of Classification Search
 CPC ........ A61L 2/26; A61L 2202/182; A61L 2/28; F16J 15/447

(Continued)

(56) References Cited

U.S. PATENT DOCUMENTS

| 4,296,862 A | 10/1981 | Armentrout et al. |
| 4,466,552 A | 8/1984 | Butterworth et al. |

(Continued)

FOREIGN PATENT DOCUMENTS

| CN | 103935620 A | 7/2014 |
| WO | 2007045943 A1 | 4/2007 |

(Continued)

OTHER PUBLICATIONS

MicroStop Accessed Jun. 5, 2019 http://www.kopaczmed.com/files/martin/kontenery.pdf.

(Continued)

*Primary Examiner* — Rafael A Ortiz
(74) *Attorney, Agent, or Firm* — Dinsmore & Shohl LLP

(57) ABSTRACT

A sterilization container for sterilizing medical instruments that includes a body defining an interior volume and a lid connected to the body and configured to seal the interior volume between the lid and the body. The lid includes an exterior filter structure including a first plurality of ridges and a first plurality of troughs formed between the first ridges. The container includes a filter assembly connected to the lid and including an interior filter structure including a second plurality of ridges and a second plurality of troughs formed between the second ridges. The first plurality of ridges of the exterior filter structure are interposed between the second plurality of ridges of the interior filter structure. The exterior and interior filter structures are configured to form longitudinal channels positioned between the lid and filter assembly to define a rectangular tortuous filter path that inhibits ingress and egress from the interior volume.

15 Claims, 19 Drawing Sheets

(58) Field of Classification Search
USPC .................. 206/363, 570; 277/303, 371, 412
See application file for complete search history.

(56) References Cited

U.S. PATENT DOCUMENTS

| | | | |
|---|---|---|---|
| 4,551,311 A * | 11/1985 | Lorenz | A61L 2/26 |
| | | | 220/360 |
| 4,661,326 A | 4/1987 | Schainholz | |
| 4,671,943 A | 6/1987 | Wahlquist | |
| 4,728,504 A | 3/1988 | Nichols | |
| 5,346,075 A | 9/1994 | Nichols et al. | |
| 5,922,162 A | 7/1999 | Brugger et al. | |
| 6,620,390 B1 | 9/2003 | Wagner | |
| 6,846,413 B1 | 1/2005 | Kadel et al. | |
| 7,132,089 B2 * | 11/2006 | Lacabanne | A61L 2/26 |
| | | | 206/436 |
| 7,914,751 B2 | 3/2011 | Oertmann | |
| 9,388,080 B2 | 7/2016 | Weisshaupt et al. | |
| 10,004,820 B2 | 6/2018 | Zwingenberger et al. | |
| 11,389,556 B2 * | 7/2022 | Henniges | A61L 2/208 |
| 2005/0161355 A1 * | 7/2005 | Matthis | A61B 50/31 |
| | | | 206/370 |
| 2007/0062830 A1 * | 3/2007 | Oertmann | A61L 2/26 |
| | | | 206/363 |
| 2010/0158751 A1 * | 6/2010 | Friderich | A61L 2/26 |
| | | | 422/27 |
| 2010/0158753 A1 * | 6/2010 | Friderich | A61L 2/26 |
| | | | 206/438 |
| 2020/0147250 A1 * | 5/2020 | Lin | A61L 2/07 |
| 2020/0147253 A1 * | 5/2020 | Spencer | A61L 2/14 |

FOREIGN PATENT DOCUMENTS

| | | |
|---|---|---|
| WO | 2014140421 A1 | 9/2014 |
| WO | 2018055086 A3 | 6/2018 |
| WO | 2019006079 A3 | 1/2019 |

OTHER PUBLICATIONS

Aygun Accessed Jun. 5, 2019 http://www.aygun.com/upload/pdf/11-full-size---bio-barrier-0a68e66.pdf.

* cited by examiner

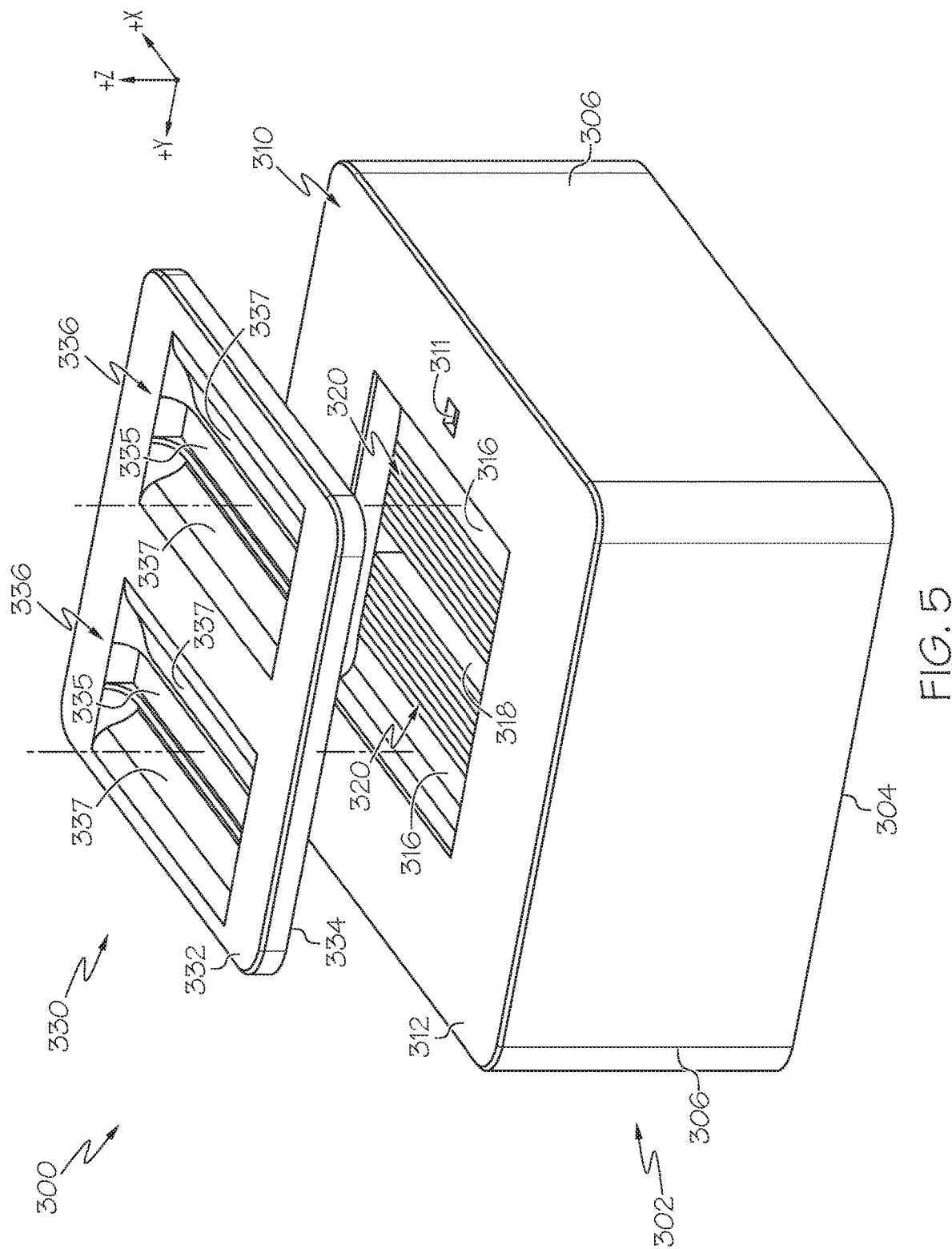

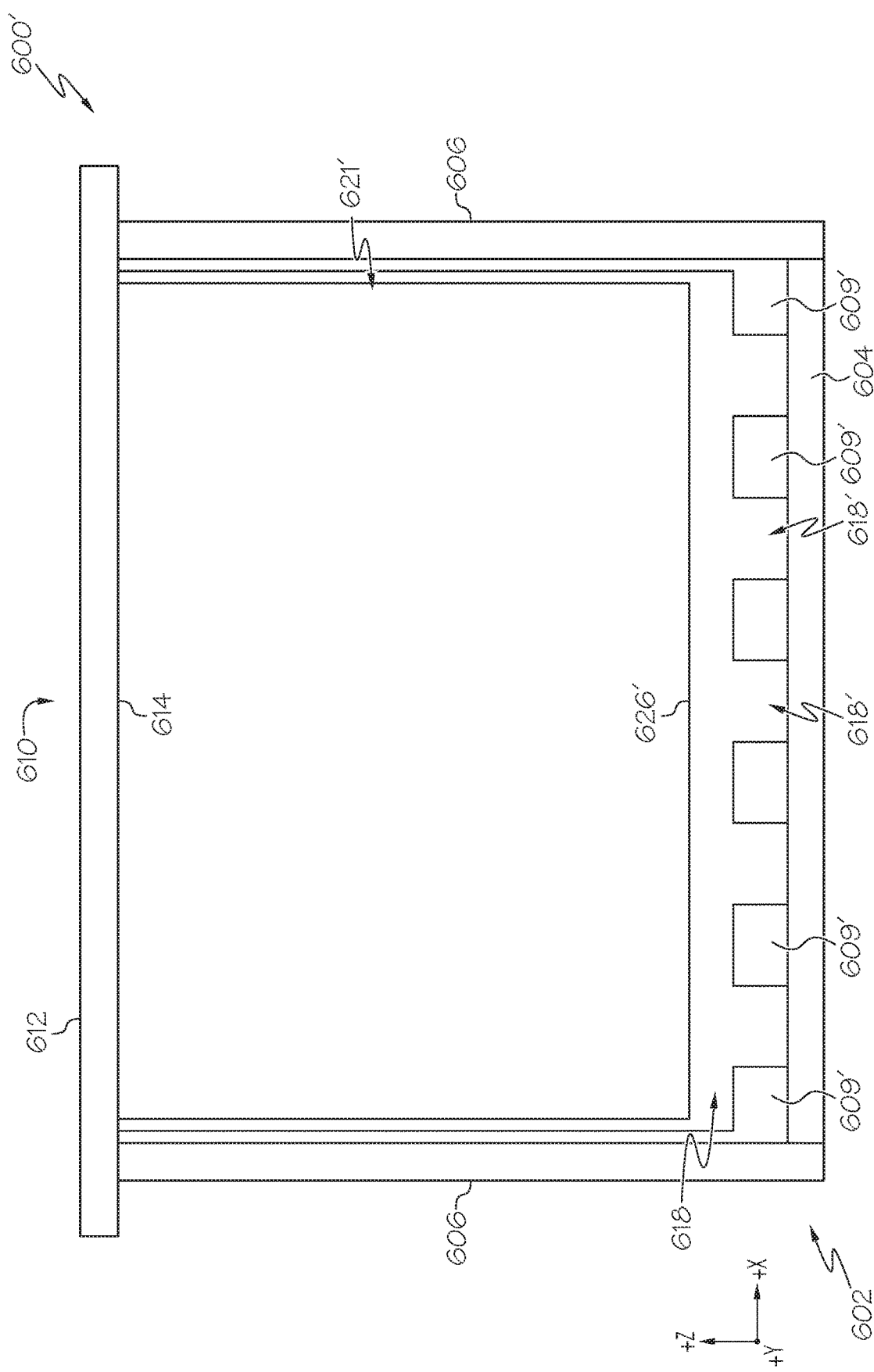

US 11,786,621 B2

REUSABLE TORTUOUS PATH FILTERS FOR STERILIZATION CONTAINERS

CROSS-REFERENCE

This application claims priority to and the benefit of U.S. Provisional Patent Application No. 62/913,446, filed Oct. 10, 2019, titled Reusable Tortuous Path Filters for Sterilization Containers, the details of which are hereby incorporated herein by reference.

TECHNICAL FIELD

The present invention generally relates to sterilization containers for maintaining sterility of medical devices stored therein, and more specifically to filters forming a tortuous path that permit ingress and egress of sterilants into the container while preventing contaminants from entering the container.

BACKGROUND

Sterilization containers are generally used to maintain a sterility of medical devices stored therein prior to use in a medical procedure. Sterilization containers may include a filter or valve system that facilitates an ingress and egress of sterilants into the container to promote a sterilization of the devices included therein. The filter or valve system further inhibits microorganisms and airborne particulates from accessing the container to prevent a contamination of the medical devices enclosed therein.

Accordingly, a need exists for a sterilization container including a tortuous path filter that is including varying structural configurations that are configured and operable to permit a flow of air and sterilant therethrough and increase a flow resistance of contaminants to prevent contamination of the medical devices stored in the container.

BRIEF DESCRIPTION OF THE DRAWINGS

FIG. 5 is a perspective view of an alternative exemplary sterilization container including a lid and a filter assembly according to one or more embodiments shown and described herein;

FIG. 9B is a side cross-sectional view of the sterilization container of FIG. 8 according to one or more embodiments shown and described herein;

DETAILED DESCRIPTION

Figure 1:
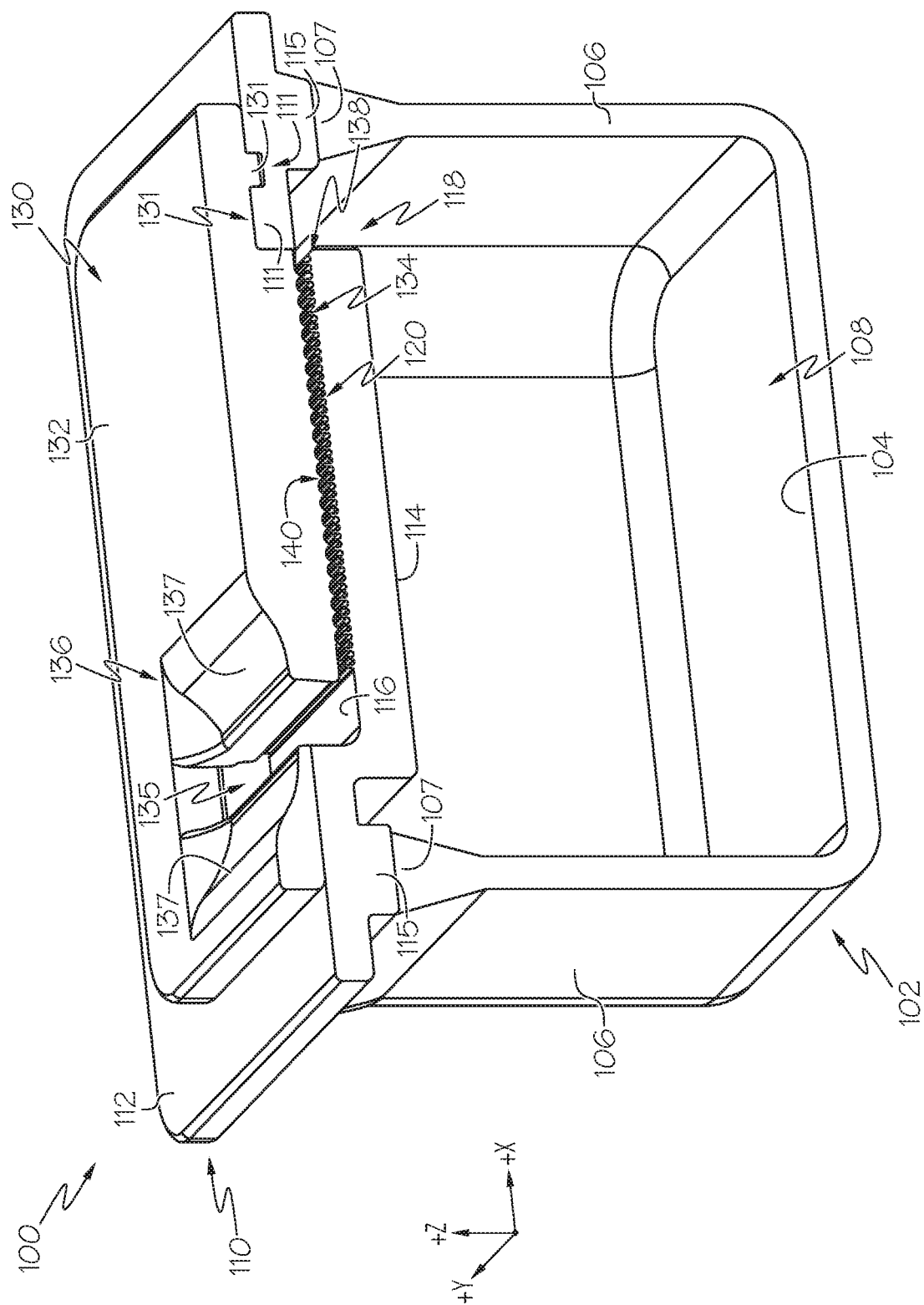
FIG. 1 is a perspective cross-sectional view of an exemplary sterilization container including a body, a lid and a filter assembly according to one or more embodiments shown and described herein.

Reference will now be made in detail to various embodiments of reusable sterilization containers including tortuous path filters for maintaining a sterility of an interior volume of the container, examples of which are illustrated in the accompanying drawings. Whenever possible, the same reference numerals will be used throughout the drawings to refer to the same or like parts. Directional terms as used herein—for example upper, lower, inner, outer, top, bottom, side, distal, and proximal—are made only with reference to the figures as drawn and are not intended to imply absolute orientation.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Unless otherwise expressly stated, it is in no way intended that any method set forth herein be construed as requiring that its steps be performed in a specific order, nor that with any apparatus specific orientations be required. Accordingly, where a method claim does not actually recite an order to be followed by its steps, or that any apparatus claim does not actually recite an order or orientation to individual components, or it is not otherwise specifically stated in the claims or description that the steps are to be limited to a specific order, or that a specific order or orientation to components of an apparatus is not recited, it is in no way intended that an order or orientation be inferred, in any respect. This holds for any possible non-express basis for interpretation, including: matters of logic with respect to arrangement of steps, operational flow, order of components, or orientation of components; plain meaning derived from grammatical organization or punctuation, and; the number or type of embodiments described in the specification.

Unless otherwise defined, all technical and scientific terms used herein have the same meaning as commonly understood by one of ordinary skill in the art to which the invention belongs. The terminology used in the description herein is for describing particular embodiments only and is not intended to be limiting. As used in the specification and appended claims, the singular forms "a," "an," and "the" are intended to include the plural forms as well, unless the context clearly indicates otherwise. Thus, for example, reference to "a" component includes aspects having two or more such components, unless the context clearly indicates otherwise.

As used herein, the terms "horizontal," "vertical," "distal," "proximal," "longitudinal" and "lateral" are relative terms only, are indicative of a general relative orientation only, and do not necessarily indicate perpendicularity. These terms also may be used for convenience to refer to orientations used in the figures, which orientations are used as a matter of convention only and are not intended as characteristic of the devices shown. The terms "interior" and "exterior" are in reference to an interior volume of the sterilization containers, with "interior" facing toward the interior volume and "exterior" facing away from the interior volume. The present invention and the embodiments thereof to be described herein may be used in any desired orientation. Moreover, horizontal and vertical walls need generally only be intersecting walls, and need not be perpendicular.

I. Sterilization Container with Rectangular Tortuous Path Filter

Figure 2:
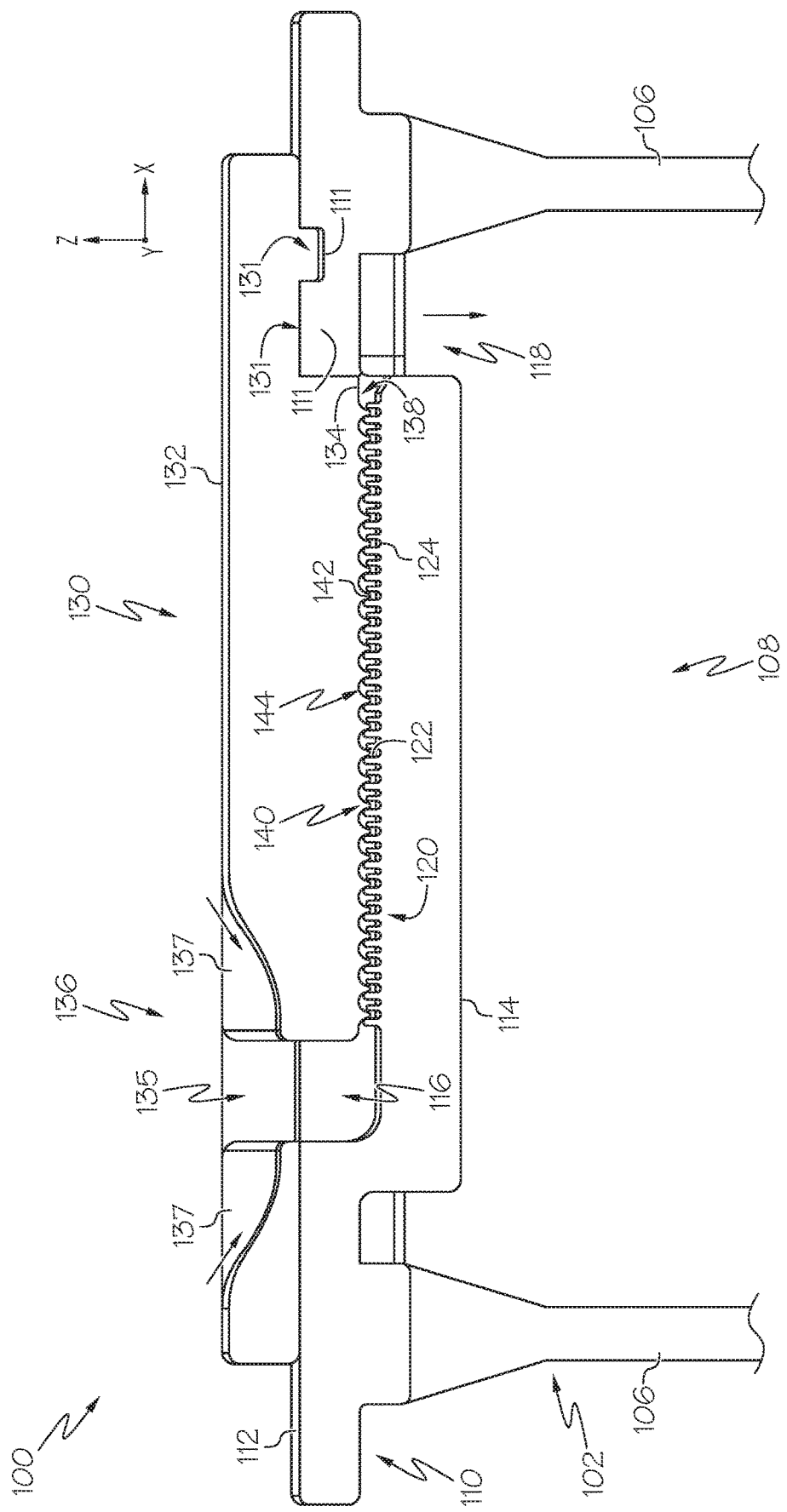
FIG. 2 is a partial cross-sectional view of the filter assembly secured to the lid of the sterilization container of FIG. 1 according to one or more embodiments shown and described herein.
Figure 3:
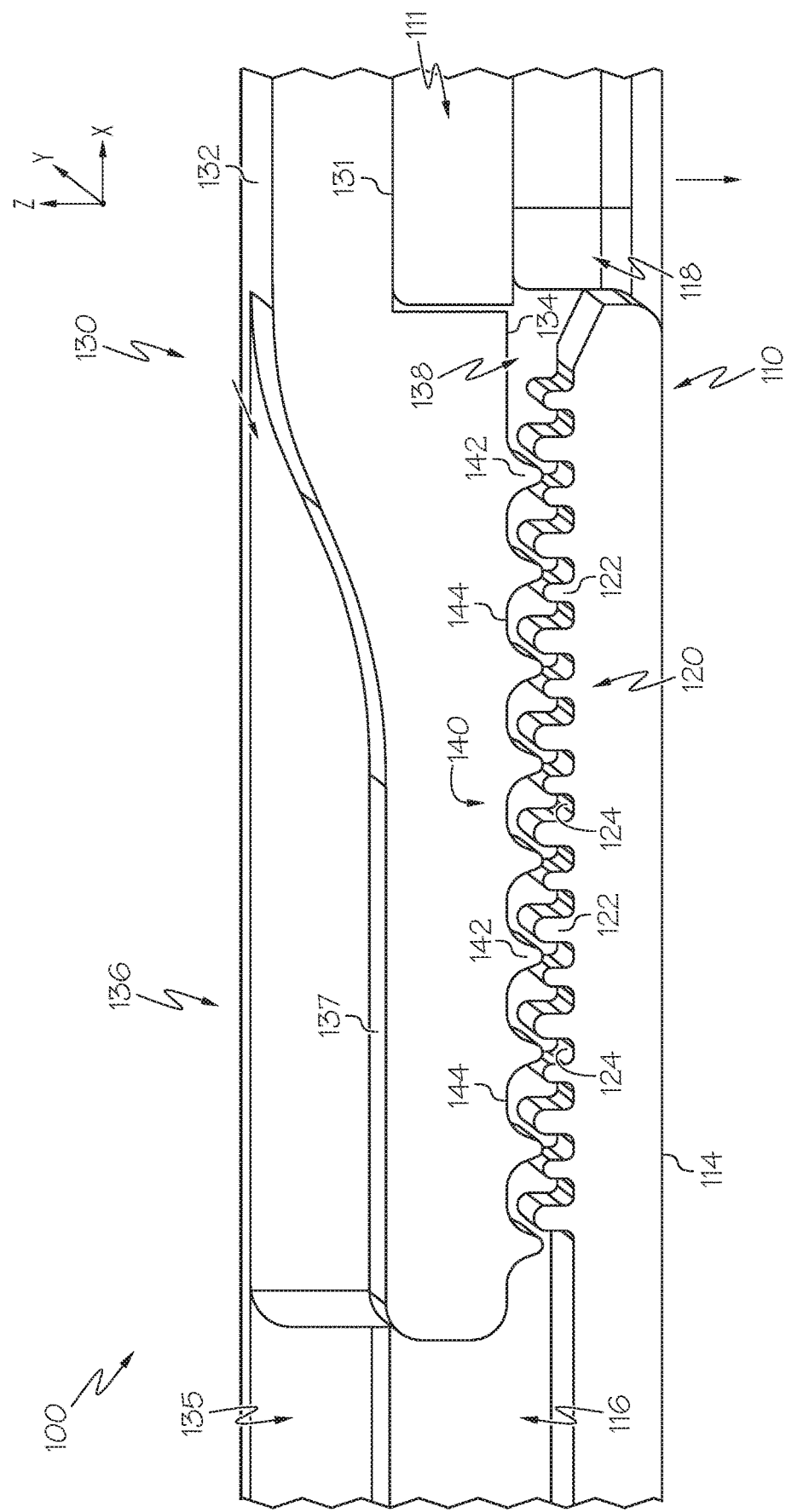
FIG. 3 is a side cross-sectional view of a tortuous path filter formed between the lid and the filter assembly of the sterilization container of FIG. 1 according to one or more embodiments shown and described herein.

Referring now to FIGS. 1-3, one embodiment of a sterilization container 100 is depicted including a rectangular tortuous path filter that is configured and operable to permit ingress and egress of airflow and sterilants therethrough while inhibiting admission of contaminants into the sterilization container 100. Specifically referring to FIG. 1, the sterilization container 100 includes a body 102, a lid 110, and a filter assembly 130. The body 102 serves as a base of the sterilization container 100 and includes a bottom wall 104 and a plurality of sidewalls 106 extending from the bottom wall 104, thereby defining an interior volume 108 therebetween. The plurality of sidewalls 106 of the body 102 extend from the bottom wall 104 to an open, top end 107 such that a longitudinal height of each of the plurality of sidewalls 106 extends between the open, top end 107 and the bottom wall 104 (i.e. in the +/−Z direction of the coordinate axes in the figures). In the embodiment, the bottom wall 104 and the plurality of sidewalls 106 are integrally formed with one another such that the body 102 is a unitary structure. However, it should be understood that in other embodiments the bottom wall 104 and/or one or more of the plurality of sidewalls 106 may be separate components secured to one another to form the body 102 of the sterilization container 100.

In the present example, the bottom wall 104 of the body 102 is generally rectangular such that the interior volume 108 formed by the bottom wall 104 and the plurality of sidewalls 106 is rectangularly shaped. Accordingly, the interior volume 108 of the body 102 is sized to receive one or more devices therein, such as, for example, medical apparatuses, instruments, and/or the like. It should be understood that in other embodiments the bottom wall 104 and the interior volume 108 formed within the body 102 may include various other shapes and/or sizes than those shown and described herein without departing from the scope of the present disclosure. In the embodiment, the body 102 is exposed at the open, top end 107 such that the plurality of sidewalls 106 extend distally from the bottom wall 104 and terminate at the open, top end 107 of the body 102. Accordingly, the interior volume 108 of the body 102 is exposed and operable to receive the one or more devices therein.

Still referring to FIG. 1, the lid 110 of the sterilization container 100 serves as a top of the sterilization container 100 and is sized and shaped in accordance with a size and shape of the body 102, such that the lid 110 is generally rectangularly shaped. In particular, the lid 110 includes an exterior surface 112 and an interior surface 114 positioned opposite of the exterior surface 112. The lid 110 further includes an engagement edge 115 extending about a perimeter of the interior surface 114. The engagement edge 115 of the lid 110 is sized and shaped relative to a size and shape of the plurality of sidewalls 106 of the body 102 such that the lid 110 is configured to be received over the body 102 and the engagement edge 115 is configured to engage the plurality of sidewalls 106 at the open, top end 107.

In this instance, the engagement edge 115 of the lid 110 abuts against and forms a seal with the open, top end 107 of the body 102 thereby enclosing the interior volume 108 between the interior surface 114 of the lid 110 and the bottom wall 104 of the body 102. It should be understood that in some embodiments the engagement edge 115 extending along the interior surface 114 of the lid 110 may include a gasket, a seal, an elastic member, and/or various other features configured to form a secured and/or airtight coupling between the lid 110 and the body 102. It should be understood that the engagement end 115 may comprise various other structural geometries than those shown and described herein without departing from a scope of the present disclosure, including, for example, channels, ribs, and/or the like. Additionally and/or alternatively, in other embodiments the open, top end 107 of the body 102 may include a gasket, seal, elastic member, and/or other feature configured to form a secured and/or airtight coupling with the lid 110.

Still referring to FIG. 1, the lid 110 of the sterilization container 100 further includes a recessed inlet 116, an outlet opening 118, and an exterior filter structure 120 disposed along the exterior surface 112. In particular, the recessed inlet 116 is positioned adjacent to a terminal end of the exterior filter structure 120 and forms a depressed surface along the exterior surface 112 of the lid 110. It should be understood that the depressed surface formed by the recessed inlet 116 is relative to a planar surface of the exterior surface 112. The outlet opening 118 of the lid 110 is positioned adjacent to another terminal end of the exterior filter structure 120 opposite of the recessed inlet 116. Accordingly, a length of the exterior filter structure 120 along the exterior surface 112 extends between the recessed inlet 116 and the outlet opening 118 such that the exterior filter structure 120 is disposed therebetween.

The outlet opening 118 forms an aperture extending between the exterior surface 112 and the interior surface 114 such that the outlet opening 118 extends through the lid 110. The exterior filter structure 120 extends laterally across a predetermined width of the exterior surface 112 of the lid 110 (i.e. in the +/−Y direction of the coordinate axes in the figures), and further extends longitudinally across a predetermined length of the exterior surface 112 of the lid 110 (i.e. in the +/−X direction of the coordinate axes in the figures). In the embodiment, the exterior filter structure 120 is integral with the lid 110 such that the exterior filter structure 120 is a unitarily-formed with the exterior surface 112. As described in greater detail herein, it should be understood that a relative position of the recessed inlet 116, the outlet opening 118, and/or the exterior filter structure 120 of the lid 110 may be located along various other surfaces and/or positions than those shown and described herein without departing from a scope of the present disclosure.

Still referring to FIG. 1, the filter assembly 130 is sized and shaped to be at least partially received within the recessed inlet 116 of the lid 110. The lid 110 further includes one or more latch elements 111 formed along the exterior surface 112 that are configured to securely fix the filter assembly 130 to the lid 110. In the present example, the lid 110 includes a pair of latch elements 111 positioned on the exterior surface 112, however, it should be understood that in other embodiments the lid 110 may include additional and/or fewer latch elements 111 thereon. For example, the pair of latch elements 111 may include a protrusion, a slot, and/or the like formed on the exterior surface 112 that are sized and shaped to engage corresponding latch elements of the filter assembly 130. It should be understood that in other embodiments the latch elements 111 of the lid 110 may include various other sizes, shapes, and/or configurations than those shown and described herein. Further, in other embodiments the lid 110 and the filter assembly 130 may form a unitary structure such that the latch elements 111 of the lid 110 and the corresponding latch elements of the filter assembly 130 may be omitted entirely.

The filter assembly 130 of the sterilization container 100 is sized and shaped in accordance with a size and shape of the recessed inlet 116 of the lid 110 such that the filter assembly 130 is generally rectangularly shaped. In particular, the filter assembly 130 includes an exterior surface 132 and an interior surface 134 positioned opposite of the exterior surface 132. The filter assembly 130 of the sterilization container 100 further includes an inlet 136 disposed along the exterior surface 132, an outlet opening 138, and an interior filter structure 140 disposed along the interior surface 134. In particular, the inlet 136 is positioned adjacent to a terminal end of the interior filter structure 140 and forms a depressed surface along the exterior surface 132 of the filter assembly 130.

Still referring to FIG. 1, it should be understood that the depressed surface formed by the inlet 136 is relative to a planar surface of the exterior surface 132 of the filter assembly 130. More specifically, the inlet 136 includes an inlet opening 135 extending through the filter assembly 130 between the exterior surface 132 and the interior surface 134. In the embodiment, a longitudinal length of the inlet opening 135 (i.e. in the +/−Y direction of the coordinate axes in the figures) extends parallel to a width of the filter assembly 130 and forms a rectangularly-shaped opening through the filter assembly 130. The inlet 136 of the filter assembly 130 further includes one or more ramps 137 positioned adjacent to the inlet opening 135. In the embodiment, a longitudinal length of the one or more ramps 137 (i.e. in the +/−Y direction of the coordinate axes in the figures) extend parallel to a width of the inlet opening 135 and forms a sloped-surface from the exterior surface 132 of the filter assembly 130 toward the inlet opening 135. In the embodiment, the interior filter structure 140 is integral with the filter assembly 130 such that the interior filter structure 140 is a unitarily-formed with the interior surface 134.

Referring now to FIG. 2, the outlet opening 138 of the filter assembly 130 is positioned adjacent to another terminal end of the interior filter structure 140 opposite of the inlet 136. Accordingly, a length of the interior filter structure 140 along the interior surface 134 extends between the inlet 136 and the outlet opening 138 such that the interior filter structure 140 is disposed therebetween. The interior filter structure 140 extends laterally across a predetermined width of the interior surface 134 of the filter assembly 130 (i.e. in the +/−Y direction of the coordinate axes in the figures), and further extends longitudinally across a predetermined length of the interior surface 134 of the filter assembly 130 (i.e. in the +/−X direction of the coordinate axes in the figures). The filter assembly 130 further includes one or more latch elements 131 formed along the interior surface 134 that are configured to securely fix the filter assembly 130 to the lid 110.

In the present example, the filter assembly 130 includes a pair of latch elements 131 positioned on the interior surface 134, however, it should be understood that in other embodiments the filter assembly 130 may include additional and/or fewer latch elements 131 thereon. The pair of latch elements 131 may include, for example, a protrusion, a slot and/or the like formed on the interior surface 134 that are sized and shaped to engage the latch elements 111 of the lid 110. In particular, the latch element 131 of the filter assembly 130, formed as a protrusion, is sized and shaped to be received within the latch element 111 of the lid 110, formed as a slot. Further, the latch element 131 of the filter assembly 130, formed as a slot, is sized and shaped to receive the latch element 111 of the lid 110, formed as a protrusion. It should be understood that in other embodiments the latch elements 131 of the filter assembly 130 may include various other sizes, shapes, and/or configurations than those shown and described herein without departing from the scope of the present disclosure.

Still referring to FIG. 2, and as briefly described above, the one or more ramps 137 of the filter assembly 130 are configured to form a sloped and/or curved surface between the exterior surface 132 and the inlet opening 135. In the present example, the filter assembly 130 of the sterilization container 100 includes a pair of ramps 137 disposed about opposing sides of the inlet opening 135, however, it should be understood that in other embodiments the filter assembly 130 may include additional and/or fewer ramps 137 than those shown and described herein. The pair of ramps 137 extends parallel to a lateral direction of the inlet opening 135 (i.e. in the +/−Y direction of the coordinate axes in the figures) and is configured to direct airflow and/or other materials, substances, and/or the like toward the inlet opening 135 of the filter assembly 130. It should be understood that in other embodiments the inlet opening 135 and/or the one or more ramps 137 of the inlet 136 may have various other sizes and/or shapes than those shown and described herein.

The exterior filter structure 120 of the lid 110 includes a plurality of ridges 122 and a plurality of troughs 124 formed therein forming an undulating pattern of ridges 122 and troughs 124. The plurality of ridges 122 and the plurality of troughs 124 may be formed as a single-piece, monolithic part of the lid 110. For example, the plurality of ridges 122 and the plurality of troughs 124 may be molded along the rest of the lid 110. Each trough 124 of the plurality of troughs 124 is formed and positioned between a pair of adjacent ridges 122 of the plurality of ridges 122, such that a size and shape of each of the troughs 124 corresponds to a relative distance between each of a pair of adjacent ridges 122. Further, a size and shape of each of the troughs 124 of the plurality of troughs 124 corresponds to a relative height of each of a pair of adjacent ridges 122 forming the trough 124.

In some embodiments, a distance between adjacent ridges 122 of the exterior filter structure 120 may vary relative to one another along the lid 110 thereby forming an irregular pattern, while in other embodiments a distance between adjacent ridges 122 of the exterior filter structure 120 may be substantially similar to one another thereby forming a regularly continuous pattern. As briefly described above, the exterior filter structure 120 is integral with the lid 110 such that the exterior filter structure 120 is a unitarily-formed with the exterior surface 112. Accordingly, the plurality of ridges 122 and the plurality of troughs 124 of the exterior filter structure 120 are integrally-formed with the exterior surface 112 such that the ridges 122 and the troughs 124 of the exterior filter structure 120 are unitary with the lid 110.

Still referring to FIG. 2, the interior filter structure 140 of the filter assembly 130 includes a plurality of ridges 142 and a plurality of troughs 144 formed therein forming an undulating pattern of ridges 142 and troughs 144. The plurality of ridges 142 and the plurality of troughs 144 may be formed as a single-piece, monolithic part of the filter assembly 130. For example, the plurality of ridges 142 and the plurality of troughs 144 may be molded along the rest of the filter assembly 130. Each trough 144 of the plurality of troughs 144 is formed and positioned between a pair of adjacent ridges 142 of the plurality of ridges 142, such that a size and shape of the troughs 144 corresponds to a relative distance between each of the pair of adjacent ridges 142. Further, a size and shape of each of the troughs 144 of the plurality of troughs 144 corresponds to a relative height of each of a pair of adjacent ridges 142 forming the trough 144.

In some embodiments, a distance between adjacent ridges 142 of the interior filter structure 140 may vary relative to one another along the filter assembly 130 thereby forming an irregular pattern, while in other embodiments the distance between adjacent ridges 142 of the interior filter structure 140 may be substantially similar to one another thereby forming a regularly continuous pattern. As briefly described above, the interior filter structure 140 is integral with the filter assembly 130 such that the interior filter structure 140 is a unitarily-formed with the interior surface 134. Accordingly, the plurality of ridges 142 and the plurality of troughs 144 of the interior filter structure 140 are integrally-formed with the interior surface 134 such that the ridges 142 and the troughs 144 of the interior filter structure 140 are unitary with the filter assembly 130.

It should be understood that the plurality of ridges 122, 142 of the filter structures 120, 140 are sized, shaped and configured to form a tortuous filter path between the filter structures 120, 140, respectively. More specifically, the tortuous filter path formed by the plurality of ridges 122, 142 of the filter structures 120, 140 includes a plurality of structural impediments between the lid 110 and the filter assembly 130 in the form of physical obstructions, barriers, hurdles and/or the like. The structural impediments formed by the plurality of ridges 122, 142 may vary based on a predetermined size and shape of the plurality of ridges 122, 142, such as, for example, a length, width, and position of each of the plurality of ridges 122, 142. Additionally, it should be understood that the plurality of troughs 124, 144 formed between the plurality of ridges 122, 142 of the filter structures 120, 140 are sized, shaped and configured to form a rectangular tortuous filter path between the filter structures 120, 140, respectively.

More specifically, the tortuous filter path formed by the plurality of troughs 124, 144 of the filter structures 120, 140 includes a plurality of structural impediments between the lid 110 and the filter assembly 130 in the form of physical cavities, recesses, depressions and/or the like. The structural impediments formed by the plurality of troughs 124, 144 may vary based on a predetermined size and shape of the troughs 124, 144 such as, for example, a depth, width, and position of each of the plurality of troughs 124, 144. In the embodiment, the tortuous filter path formed by the plurality of troughs 124, 144 of the filter structures 120, 140 is a rectangular tortuous filter path including a plurality of longitudinal structural impediments between the lid 110 and the filter assembly 130. For example, the plurality of longitudinal structural impediments forming the rectangular tortuous filter path between the filter structures 120, 140 may include longitudinal and/or elongated cavities, recesses and/or depressions positioned in a parallel arrangement relative to one another.

Still referring to FIG. 2, with the lid 110 secured to the body 102 and the filter assembly 130 positioned over the lid 110, the interior filter structure 140 is disposed over the exterior filter structure 120 thereby forming the tortuous path filter therebetween. In other words, the exterior filter structure 120 is configured to mesh with the interior filter structure 140 in response to the lid 110 receiving the filter assembly 130 thereon. In particular, the plurality of ridges 122 of the exterior filter structure 120 extends into and are received within the plurality of troughs 144 of the interior filter structure 140. Further, the plurality of ridges 142 of the interior filter structure 140 extend into and are received within the plurality of troughs 124 of the exterior filter structure 120. In this instance, a rectangular tortuous filter path is formed therebetween including a series of longitudinal, elongated, and/or rectangular channels positioned between the lid 110 and the filter assembly 130.

Additionally, the pair of latch elements 111 of the lid 110 engages the pair of latch elements 131 of the filter assembly 130, thereby aligning a position of the recessed inlet 116 of the lid 110 with a position of the inlet 136 of the filter assembly 130, and more particularly the inlet opening 135. In this instance, the inlet opening 135 and the recessed inlet 116 collectively form an ingress point for the rectangular tortuous filter path formed by the coupling of the filter structures 120, 140. The outlet opening 118 of the lid 110 is further aligned with the outlet opening 138 of the filter assembly 130 such that the outlet openings 118, 138 collectively form an egress point for the rectangular tortuous path filter formed by the joinder of the filter structures 120, 140. In the embodiment, a size and shape of the ingress point formed by the inlet opening 135 and the recessed inlet 116 is substantially similar to a size and shape of the egress point formed by the outlet openings 118, 138. Accordingly, the sterilization container 100 of the embodiment is configured to form a consistent inlet cross-sectional area and outlet cross-sectional area between the pair of filter structures 120, 140. It should be understood that in other embodiments the size and shape of the ingress point at the inlet opening 135 and the recessed inlet 116 may vary relative to the size and shape of the egress point at the outlet openings 118, 138 without departing from a scope of the present disclosure.

Referring now to FIG. 3, in this embodiment, the plurality of ridges 122 of the exterior filter structure 120 extend at varying heights relative to one another. In some embodiments, the plurality of ridges 122 may extend at alternating lengths and/or heights in a predetermined pattern while, in other embodiments, the relative heights of the plurality of ridges 122 may be arbitrary and/or random. It should be understood that in other embodiments the plurality of ridges 122 of the exterior filter structure 120 may extend at similar lengths relative to one another. In the present example, the plurality of ridges 122 of the exterior filter structure 120 extend at varying lengths in an alternating pattern relative to an adjacent ridge 122 of the exterior filter structure 120. A length and/or thickness of the plurality of ridges 122 is determinative of a size and shape of the plurality of troughs 124 of the exterior filter structure 120 formed therebetween. However, it should be understood that the plurality of troughs 124 of the exterior filter structure 120 may extend at varying depths relative to one another in embodiments where the plurality of ridges 122 include similar heights and/or lengths along the exterior filter structure 120. In some embodiments, the heights of the plurality of ridges 122 may be such that they extend into the plurality of troughs 124 of the lid 110.

The plurality of ridges 142 of the interior filter structure 140 extend at similar heights and lengths relative to one another. In other embodiments, the plurality of ridges 142 may extend at varying heights and lengths in a predetermined pattern, and the relative heights and lengths of the plurality of ridges 142 may be arranged in an arbitrary (i.e. random) pattern. In the present example, the plurality of ridges 142 of the interior filter structure 140 extend at similar heights in a uniform pattern relative to an adjacent ridge 142 of the interior filter structure 140. A length and/or thickness of the plurality of ridges 142 in the longitudinal direction (i.e. in the +/−X direction of the coordinate axes in the figures) is determinative of a size and shape of the plurality of troughs 144 of the interior filter structure 140 formed therebetween. However, it should be understood that the plurality of troughs 144 of the interior filter structure 140 may extend at varying depths (i.e. in the +/−Z direction of the coordinate axes in the figures) relative to one another in embodiments where the plurality of ridges 142 include similar heights and/or lengths along the interior filter structure 140 (i.e. in the +/−Z direction of the coordinate axes in the figures). In the illustrated embodiment, the plurality of troughs 144 have lengths (i.e. in the +/−X direction of the coordinate axes in the figures) such that the plurality of troughs 144 extend across multiple (e.g., two or more) ridges 142 of the plurality of ridges 142. In some embodiments, the heights of the plurality of ridges 142 (i.e. in the +/−Z direction of the coordinate axes in the figures) may be such that they extend into the plurality of troughs 144 of the filter assembly 130.

Still referring to FIG. 3, the recessed inlet 116 of the lid 110 is sized in accordance with the inlet opening 135 of the filter assembly 130. As briefly described above, the lid 110 is configured to align the recessed inlet 116 with the inlet opening 135 of the filter assembly 130 in response to the engagement of the latch elements 111 of the lid 110 with the corresponding latch elements 131 of the filter assembly 130. Further, the outlet opening 118 of the lid 110 is positioned is sized in accordance with the outlet opening 138 of the filter assembly 130. Accordingly, the lid 110 is further configured to align the outlet opening 118 of the lid 110 with the outlet opening 138 of the filter assembly 130 in response to the engagement of the latch elements 111 of the lid 110 with the corresponding latch elements 131 of the filter assembly 130.

With the filter assembly 130 secured to the lid 110 and the body 102 enclosed therein, an ingress and egress into the interior volume 108 of the body 102 (see FIG. 1) is facilitated by the inlets 116, 136, the rectangular tortuous filter path formed between the filter structures 120, 140, and the outlet openings 118, 138. In other words, access to the interior volume 108 of the body 102 (see FIG. 1) is inhibited (i.e. limited) as the filter structures 120, 140 form a series of longitudinal, elongated, and/or rectangular channels that are configured to form a rectangular tortuous filter path including a plurality of structural impediments. In particular, the plurality of troughs 144 of the interior filter structure 140 are sized, shaped and configured to receive the plurality of ridges 122 of the exterior filter structure 120, and the plurality of troughs 124 of the exterior filter structure 120 are sized, shaped and configured to receive the plurality of ridges 142 of the interior filter structure 140.

Still referring to FIG. 3, with the filter assembly 130 of the sterilization container 100 coupled to the lid 110 and the filter structures 120, 140 meshed with one another, the rectangular tortuous path filter formed therebetween is configured to facilitate an ingress and egress of certain materials therethrough and into the interior volume 108 (see FIG. 1) while preventing other materials from traversing therethrough. In particular, the rectangular tortuous path filter formed by the filter structures 120, 140 is configured to allow an ingress and egress of sterilant from the inlet opening 135 and the recessed inlet 116, and through the outlet openings 118, 138, and further configured to inhibit microorganisms and airborne particulate from traversing through the filter structures 120, 140 and into the outlet openings 118, 138. In other words, the rectangular tortuous filter path formed by the filter structures 120, 140 is configured to decrease flow resistance of air and sterilant while increasing flow resistance of contaminants into the interior volume 108 of the body 102.

In other embodiments, the exterior filter structure 120 and/or the interior filter structure 140 may be preassembled with one another prior to coupling the filter assembly 130 to the lid 110 without departing from a scope of the present disclosure. In this instance, the filter assembly 130 includes the pair of filter structures 120, 140 assembled to one another, with the plurality of ridges 122 and the plurality of troughs 124 meshed with the corresponding plurality of ridges 142 and the plurality of troughs 144, respectively, prior to coupling the filter assembly 130 with the lid 110. Accordingly, the filter assembly 130 is configured to be selectively coupled to the lid 110, and more specifically the connected pair of filter structures 120, 140 is configured to be assembled onto the lid 110. In the embodiment, the exterior filter structure 120 is not integrally-formed with the lid 110. In other words, the exterior filter structure 120 and the interior filter structure 140 are configured to engage the lid 110, such that the pair of filter structures 120, 140 is removably secured to at least one of the exterior surface 112 and/or the interior surface 114.

It should be understood that in other embodiments one or more filter structures may be integrally formed and/or removably assembled onto the bottom wall 104 of the body 102 without departing from a scope of the present disclosure. In this instance, the sterilization container 100 may include the exterior filter structure 120, the interior filter structure 140, and an additional one or more filter structures along the bottom wall 104 of the body 102. Accordingly, the pair of filter structures 120, 140 may be configured to facilitate an ingress and egress into the interior volume 108 of the body 102 and the additional one or more filter structures along the bottom wall 104 of the body 102 may be further configured to facilitate an ingress and egress into the interior volume 108. Alternatively, as described in greater detail herein, in some embodiments a filter structure may be positioned along the interior surface 114 of the lid 110 and/or an exterior surface 132 of the filter assembly 130.

II. Alternative Sterilization Container with Rectangular Tortuous Path Filter

Figure 4:
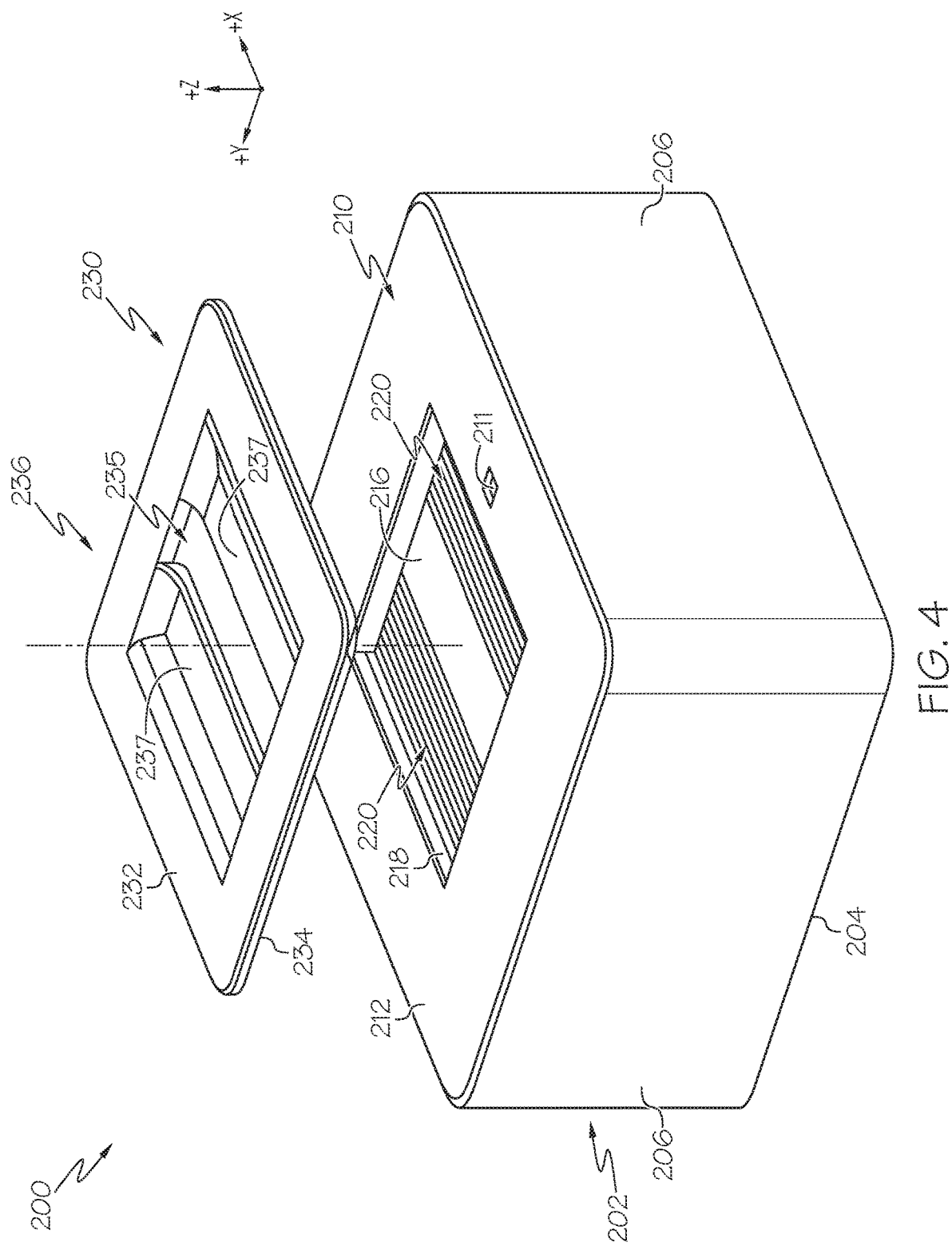
FIG. 4 is a perspective view of an alternative exemplary sterilization container including a lid and a filter assembly according to one or more embodiments shown and described herein.

FIG. 4 schematically depicts an alternative embodiment of a sterilization container 200 that is substantially similar to the sterilization container 100 shown and described above. Except as otherwise described below, the sterilization container 200 may be configured and operable like the sterilization container 100. For instance, the sterilization container 200 includes a body 202 formed by a bottom wall 204 and a plurality of sidewalls 206 thereby defining an interior volume therein. The sterilization container 200 includes a lid 210 that is secured to the body 202 and includes an exterior surface 212 and an interior surface opposite of the exterior surface 212. The exterior surface 212 of the lid 210 includes one or more latch elements 211, a recessed inlet 216, and a pair of outlet openings 218 disposed thereon. As similarly described in greater detail above with respect to the lid 110 of the sterilization container 100, the one or more latch elements 211 are sized, shaped and configured to securely couple the lid 210 to one or more other components of the sterilization container 200, such as a filter assembly 230. Additionally, the interior volume of the body 202 is generally sized to receive one or more devices therein, such as, for example, medical apparatuses, instruments, and/or the like.

The exterior surface 212 of the lid 210 further includes a pair of filter structures 220 disposed about the recessed inlet 216, wherein each of the filter structures 220 extends along the exterior surface 212 and is positioned between the recessed inlet 216 and at least one of the pair of outlet openings 218. In particular, the recessed inlet 216 is positioned adjacent to terminal ends of the pair of filter structures 220 and forms a depressed surface along the exterior surface 212 of the lid 210. It should be understood that the depressed surface formed by the recessed inlet 216 is relative to a planar surface of the exterior surface 212. Each of the pair of outlet openings 218 of the lid 210 is positioned adjacent to a terminal end of at least one of the pair of filter structures 220 opposite of the recessed inlet 216. It should be understood that the pair of filter structures 220 of the lid 210 include a plurality of ridges and a plurality of troughs as similarly described and shown above with respect to the exterior filter structure 120 of the lid 110.

Still referring to FIG. 4, the sterilization container 200 further includes a filter assembly 230 having an exterior surface 232 and an interior surface 234 positioned opposite of the exterior surface 232. The exterior surface 232 of the filter assembly 230 includes an inlet 236 disposed thereon, and in particular the inlet 236 includes an inlet opening 235 and one or more ramps 237 disposed about the inlet opening 235. In the embodiment, a longitudinal length of the inlet opening 235 of the inlet 236 extends parallel to a width of the filter assembly 230 (i.e. in the +/−X direction of the coordinate axes in the figures) and forms a rectangularly-shaped opening through the filter assembly 230. In the present example, the inlet 236 of the filter assembly 230 includes a pair of ramps 237 positioned along opposing sides of the inlet opening 235. The pair of ramps 237 of the filter assembly 230 is configured to form a curved surface between the exterior surface 232 and the inlet opening 235.

It should be understood that in other embodiments the filter assembly 230 may include additional and/or fewer ramps 237 than those shown and described herein without departing from the scope of the present disclosure. The pair of ramps 237 extends parallel to a length of the inlet opening 235 (i.e. in the +/−X direction of the coordinate axes in the figures) and is configured to direct airflow and/or other materials, substances, and/or the like toward the inlet opening 235. It should be understood that in other embodiments the inlet opening 235 and/or the one or more ramps 237 of the inlet 236 may have various other sizes and/or shapes than those shown and described herein.

Although not shown, it should be understood that the filter assembly 230 of the sterilization container 200 further includes a pair of filter structures, a pair of outlet openings, and one or more latch elements disposed on the interior surface 234 of the filter assembly 230. Except as otherwise described below, it should be understood that the filter structures, outlet openings, and latch elements of the filter assembly 230 are substantially similar and configured like the interior filter structure 140, the outlet opening 138, and the latch element 131 of the filter assembly 130 shown and described above, respectively. In particular, the pair of outlet openings are positioned along the interior surface 234 at terminal ends of each of the pair of filter structures of the filter assembly 230 such that the outlet openings of the filter assembly 230 are aligned with the pair of outlet openings 218 of the lid 210 when the filter assembly 230 is received over and coupled to the lid 210 of the sterilization container 200. It should be understood that the pair of filter structures of the filter assembly 230 include a plurality of ridges and a plurality of troughs as similarly described and shown above with respect to the interior filter structure 140 of the filter assembly 130. The plurality of ridges and the plurality of troughs in each of the filter structures of the filter assembly 230 are configured to mesh with the plurality of ridges and the plurality of troughs of the pair of filter structures 220 of the lid 210.

Still referring to FIG. 4, securing the interior surface 234 of the filter assembly 230 onto the exterior surface 212 of the lid 210 via the engagement of the corresponding latch elements 211 of the lid 210 and the latch element of the filter assembly 230, respectively, provides a coupling of the filter structures 220 of the lid 210 with the filter structures of the filter assembly 230. In this instance, a pair of tortuous path filters is formed between the lid 210 and the filter assembly 230, and in particular a pair of rectangular tortuous path filters due a rectangularly-shaped profile of the filter structures 220 of the lid 210 and a rectangularly-shaped profile of the filter structures of the filter assembly 230. The sterilization container 200 includes a single ingress point into the tortuous path filters formed by the filter structures 220 of the lid 210 and the filter structures of the filter assembly 230 at the inlet opening 235 and the recessed inlet 216, respectively. Additionally, the sterilization container 200 includes multiple egress points from the tortuous path filters via the pair of outlet openings 218 of the lid 210 and the pair of outlet openings of the filter assembly 230 aligned therewith, respectively.

III. Alternative Sterilization Container with Rectangular Tortuous Path Filter

Referring now to FIG. 5, an alternative embodiment of a sterilization container 300 that is substantially similar to the sterilization container 100, 200 shown and described above is schematically depicted. Except as otherwise described below, the sterilization container 300 may be configured and operable like the sterilization containers 100, 200. For instance, the sterilization container 300 includes a body 302 formed by a bottom wall 304 and a plurality of sidewalls 306 thereby defining an interior volume therein. The sterilization container 300 includes a lid 310 that is secured to the body 302 and includes an exterior surface 312 and an interior surface opposite of the exterior surface 312. The exterior surface 312 of the lid 310 includes one or more latch elements 311, a pair of recessed inlets 316, and an outlet opening 318 disposed thereon. As similarly described in greater detail above with respect to the lid 110 of the sterilization container 100, the one or more latch elements 311 are sized, shaped and configured to securely couple the lid 310 to one or more other components of the sterilization container 300, such as a filter assembly 330. Additionally, the interior volume of the body 302 is generally sized to receive one or more devices therein, such as, for example, medical apparatuses, instruments, and/or the like.

The exterior surface 312 of the lid 310 further includes a pair of filter structures 320 disposed about the outlet opening 318, wherein each of the filter structures 320 extends along the exterior surface 312 and is positioned between the outlet opening 318 and at least one of the recessed inlets 316. In particular, the pair of recessed inlets 316 is positioned adjacent to terminal ends of the pair of filter structures 320 and form a depressed surface along the exterior surface 312 of the lid 310. It should be understood that the depressed surfaces formed by each of the pair of recessed inlets 316 are relative to a planar surface of the exterior surface 312. The outlet opening 318 of the lid 310 is positioned adjacent to a terminal end of both of the pair of filter structures 320 opposite of the pair of recessed inlets 316. It should be understood that the pair of filter structures 320 of the lid 310 include a plurality of ridges and a plurality of troughs as similarly described and shown above with respect to the exterior filter structure 120 of the lid 110.

Still referring to FIG. 5, the sterilization container 300 further includes a filter assembly 330 having an exterior surface 332 and an interior surface 334 positioned opposite of the exterior surface 332. The exterior surface 332 of the filter assembly 330 includes a pair of inlets 336 disposed thereon corresponding to the pair of recessed inlets 316 of the lid 310. In particular, the pair of inlets 336 of the filter assembly 330 each includes an inlet opening 335 and one or more ramps 337 disposed about the inlet opening 335. In the embodiment, a longitudinal length of each of the inlet openings 335 of the pair of inlets 336 extends parallel to a width of the filter assembly 330 (i.e. in the +/−X direction of the coordinate axes in the figures) and forms a rectangularly-shaped opening through the filter assembly 330. In the present example, each of the pair of inlets 336 of the filter assembly 330 includes a pair of ramps 337 positioned along opposing sides of the inlet openings 335, respectively. Each of the pair of ramps 337 of the pair of inlets 336 are configured to form a curved surface between the exterior surface 332 and the corresponding inlet opening 335.

It should be understood that in other embodiments the filter assembly 330 may include additional and/or fewer ramps 337 than those shown and described herein without departing from the scope of the present disclosure. The pair of ramps 337 extends parallel to a length of the inlet openings 335 and is configured to direct airflow and/or other materials, substances, and/or the like toward the inlet openings 335. It should be understood that in other embodiments the inlet openings 335 and/or the one or more ramps 337 of the inlets 336 may have various other sizes and/or shapes than those shown and described herein.

Although not shown, it should be understood that the filter assembly 330 of the sterilization container 300 further includes a pair of filter structures, a pair of outlet openings, and one or more latch elements disposed on the interior surface 334 of the filter assembly 330. Except as otherwise described below, it should be understood that the filter structures, outlet openings, and latch elements of the filter assembly 330 are substantially similar and configured like the interior filter structure 140, the outlet opening 138, and the latch element 131 of the filter assembly 130 shown and described above, respectively. In particular, the pair of outlet openings are positioned along the interior surface 334 at terminal ends of each of the pair of filter structures of the filter assembly 330 such that the outlet openings of the filter assembly 330 are aligned with the outlet opening 318 of the lid 310 when the filter assembly 330 is received over and coupled to the lid 310 of the sterilization container 300. It should be understood that the pair of filter structures of the filter assembly 330 include a plurality of ridges and a plurality of troughs as similarly described and shown above with respect to the interior filter structure 140 of the filter assembly 130. The plurality of ridges and the plurality of troughs in each of the filter structures of the filter assembly 330 are configured to mesh with the plurality of ridges and the plurality of troughs of the pair of filter structures 320 of the lid 310.

Still referring to FIG. 5, securing the interior surface 334 of the filter assembly 330 onto the exterior surface 312 of the lid 310 via the engagement of the corresponding latch elements 311 of the lid 310 and the latch element of the filter assembly 330, respectively, provides a coupling of the filter structures 320 of the lid 310 with the filter structures of the filter assembly 330. In this instance, a pair of tortuous path filters is formed between the lid 310 and the filter assembly 330, and in particular a pair of rectangular tortuous path filters due a rectangularly-shaped profile of the filter structures 320 of the lid 310 and a rectangularly-shaped profile of the filter structures of the filter assembly 330. The sterilization container 300 includes multiple ingress points into the tortuous path filters formed by the filter structures 320 of the lid 310 and the filter structures of the filter assembly 330 at the inlet openings 335 and recessed inlets 316, respectively. Additionally, the sterilization container 300 includes a single egress point from the tortuous path filters via the outlet opening 318 of the lid 310 and the pair of outlet openings of the filter assembly 330 aligned therewith, respectively.

IV. Modular Lid with Rectangular Tortuous Path Filter

Referring now to FIGS. 6A-6D, an alternative embodiment of a modular filter lid assembly 430 that is substantially similar to the filter assembly 130, 230, 330 shown and described above is schematically depicted. Except as otherwise described below, the modular filter lid assembly 430 may be configured and operable like the filter assembly 130, 230, 330. Accordingly, it should be understood that the modular filter lid assembly 430 of the present example may be readily incorporated into the sterilization containers 100, 200, 300 described above, and more particularly the modular filter lid assembly 430 may be readily utilized with and/or in lieu of the lids 110, 210, 310 shown and described above. In many respects, the modular filter lid assembly 430 functions substantially similar to the filter assembly 130, 230, 330 described in detail above such that a version of the sterilization containers 100, 200, 300 equipped with the modular filter lid assembly 430 of the present example may be configured and operable similar to the sterilization containers 100, 200, 300 equipped with the filter assembly 130, 230, 330 except for the differences discussed herein.

Figure 6B:
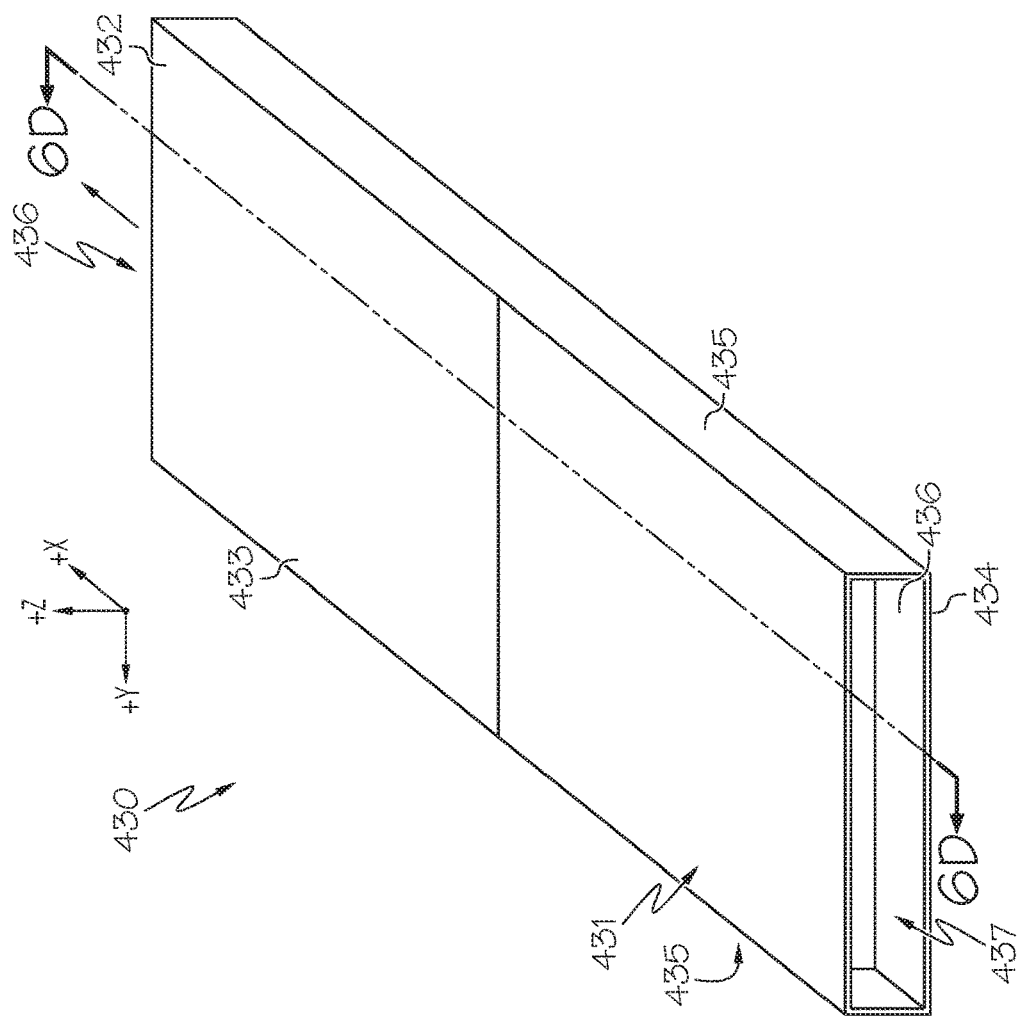
FIG. 6B is a perspective view of the lid of FIG. 6A, with the lid in an expanded state according to one or more embodiments shown and described herein.
Figure 6A:
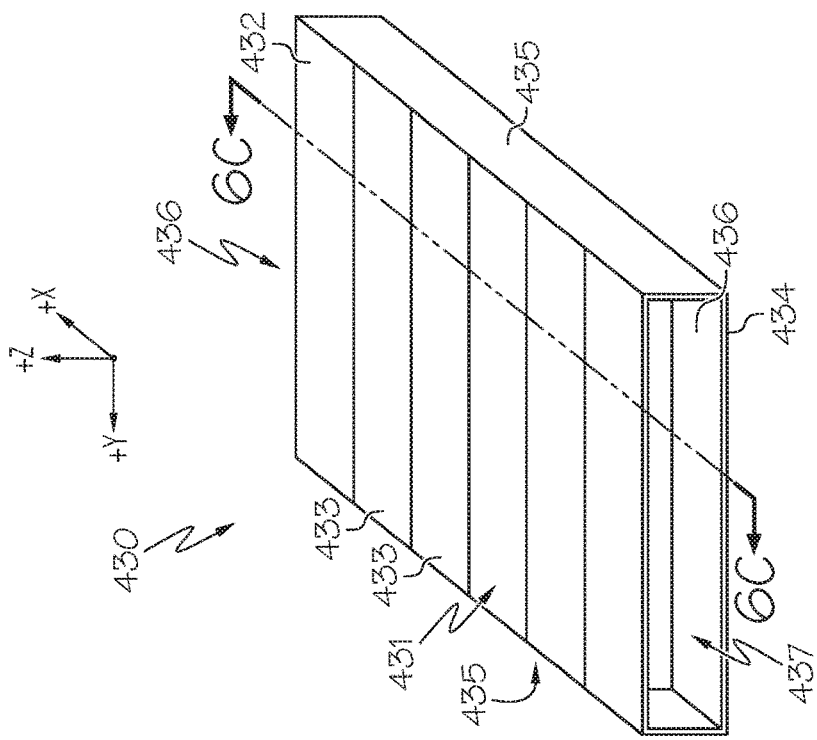
FIG. 6A is a perspective view of another exemplary lid for a sterilization container, with the lid in a compact state according to one or more embodiments shown and described herein.

Referring specifically to FIG. 6A, the modular filter lid assembly 430 includes a modular body 431 defined by an exterior surface 432, an interior surface 434, a pair of sidewalls 435 and a pair of opposing ends 436. The modular body 431 includes a lateral width extending between the pair of sidewalls 435 (i.e. in the +/−Y direction of the coordinate axes in the figures) and a longitudinal length extending between the pair of opposing ends 436 (i.e. in the +/−X direction of the coordinate axes in the figures). The modular body 431 is formed of a plurality of movable body segments 433 positioned between the pair of opposing ends 436. Each of the plurality of movable body segments 433 of the modular body 431 is configured to extend outwardly relative to one another to selectively form a plurality of configurations, shapes, profiles, orientations, and/or the like of the modular filter lid assembly 430. In other words, the plurality of movable body segments 433 are modular such that each of the movable body segments 433 are selectively expandable and/or collapsible relative to one another in the +/−X direction of FIG. 6A.

As described in greater detail herein, a lateral width of the modular body 431 extending between the pair of sidewalls 435 (i.e. in the +/−Y direction of the coordinate axes in the figures) is fixed and a longitudinal length of the modular body 431 extending between the pair of opposing ends 436 is selectively adjustable (i.e. in the +/−X direction of the coordinate axes in the figures). At least one of the pair of opposing ends 436 of the modular body 431 includes an inlet 437 formed therein. The inlet 437 extends into the modular body 431 of the modular filter lid assembly 430 and is configured to facilitate access to a tortuous path filter of the modular filter lid assembly 430 disposed within the modular body 431. The modular body 431 of the modular filter lid assembly 430 is depicted in a first, compacted state with the pair of opposing ends 436 separated from one another by a first distance. In this instance, the tortuous path filter formed within the modular body 431 has a first configuration based on the first, compacted state of the modular body 431.

Referring now to FIG. 6B, the modular body 431 of the modular filter lid assembly 430 is depicted in a second, expanded state with the pair of opposing ends 436 separated from one another by a second distance that is larger than the first distance shown and described above. In this instance, the tortuous path filter formed within the modular body 431 has a second configuration based on the second, expanded state of the modular body 431. With the modular body 431 formed of a plurality of movable body segments 433, the modular body 431 of the modular filter lid assembly 430 is configured to selectively transition between the first, compacted state and the second, expanded state in response to an outward expansion of each of the plurality of movable body segments 433. For example, the pair of opposing ends 436 of the modular body 431 may be physically manipulated to manually adjust (i.e. increase and/or decrease) a separation distance positioned therebetween, thereby modifying a longitudinal length of the modular body 431 (i.e. in the +/−X direction of the coordinate axes in the figures). As described in greater detail herein, each of the plurality movable body segments 433 of the modular body 431 are configured to movably expand outwardly and/or collapse inwardly relative one another in response to the physical manipulation of the pair of opposing ends 436 of the modular body 431 in the +/−X direction of FIG. 6A.

By way of illustrative example, in some embodiments the plurality of movable body segments 433 of the modular body 431 are structurally configured to stack atop one another when the modular body 431 is in the first, compacted state, and alternatively unstack relative to one another when the modular body 431 transitions to the second, expanded state. Alternatively, in other embodiments the plurality of movable body segments 433 are configured to be slidably received within an adjacent movable body segment 433 when in the first, compacted state, and alternatively translate externally from an adjacent movable body segment 433 when the modular body 431 transitions to the second, expanded state. In further embodiments, the plurality of movable body segments 433 of the modular body 431 may be individually foldable over itself and/or an adjacent movable body segment 433 when in the first, compacted state, and further unfoldable when the modular body 431 transitions to the second, expanded state. By way of further example, in embodiments the plurality of movable body segments 433 may formed of flexibly depressible materials, such as, for example, polystyrene. In this instance, each of the plurality of movable body segments 433 may be selectively depressed when in the first, compacted state, and alternatively expanded outwardly when the modular body 431 transitions to the second, expanded state.

Accordingly, the plurality of movable body segments 433 are configured to be selectively adjusted to expand and/or collapse the modular body 431 to increase and/or decrease a longitudinal length defined between the pair of opposing ends 436 (i.e. in the +/−X direction of the coordinate axes in the figures). It should be understood that the plurality of movable body segments 433 of the modular body 431 may be configured to transition from the first, compacted state to the second, expanded state in various suitable manners without departing from the scope of the present disclosure. It should further be understood that with a tortuous path filter disposed within the modular body 431, the tortuous path filter is configured to selectively expand and/or collapse simultaneously with a corresponding expansion and/or collapse of the plurality of movable body segments 433. In other embodiments, the modular body 431 of the modular filter lid assembly 430 may be configured and operable to selectively adjust the plurality of movable body segments 433 to expand and/or collapse a lateral width of the modular filter lid assembly 430 defined between the pair of opposing sidewalls 435 in the +/−Y direction of FIG. 6B, a thickness defined between the exterior surface 432 and the interior surface 434, and/or the like.

Figure 6C:
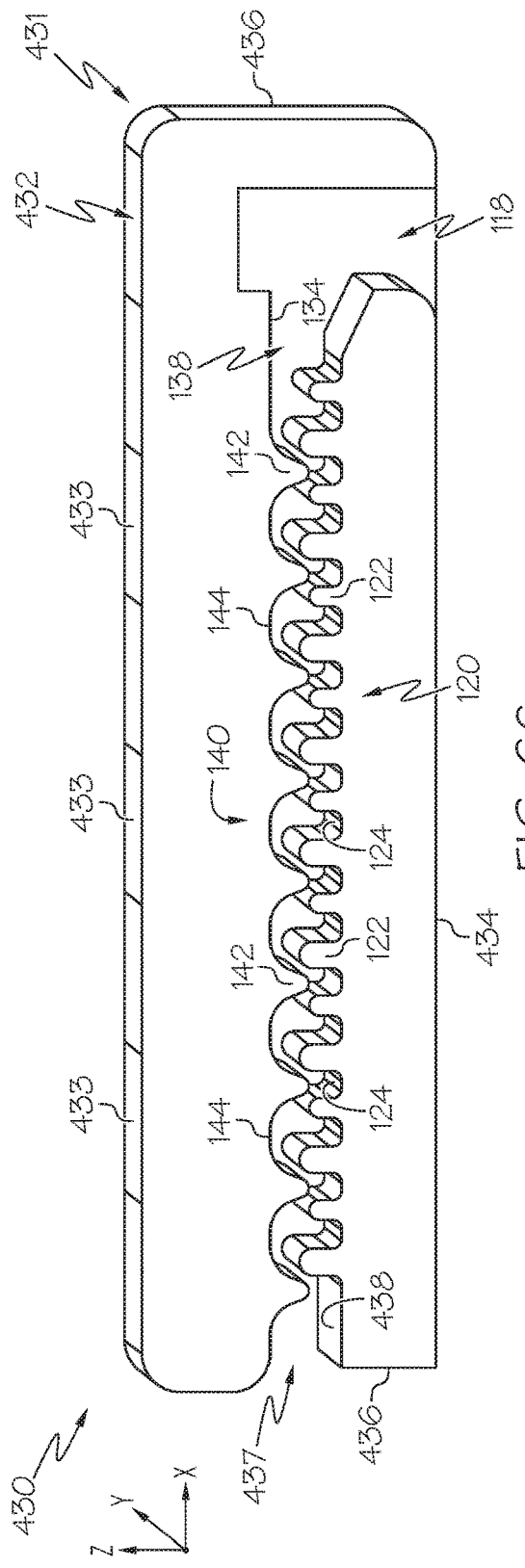
FIG. 6C is a cross-sectional view of the lid of FIG. 6A in the compact state and including a tortuous path filter disposed therein according to one or more embodiments shown and described herein.
Figure 6D:
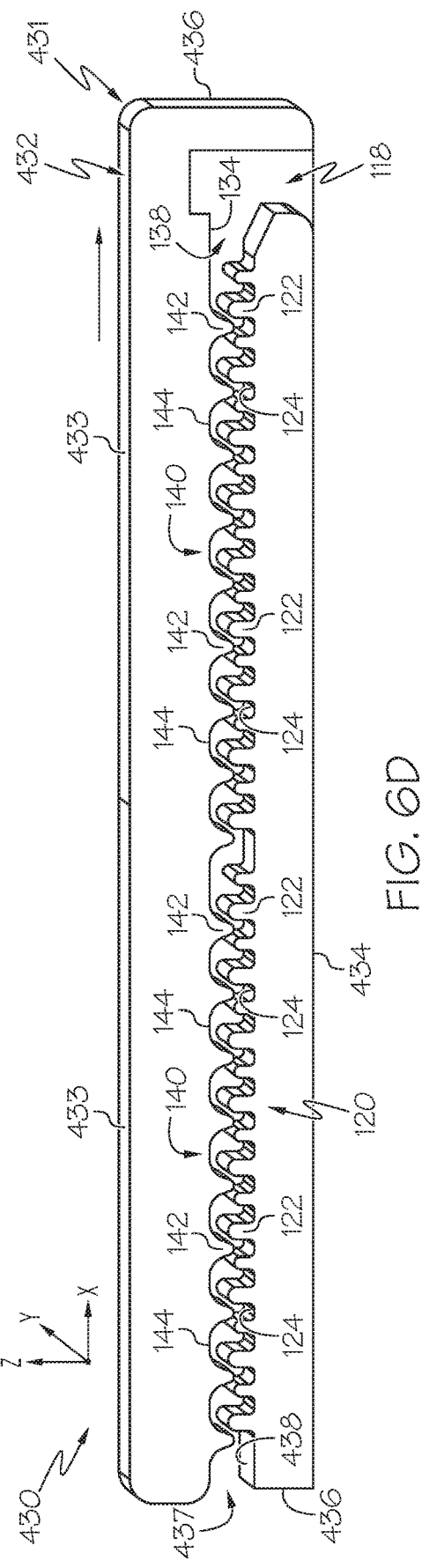
FIG. 6D is a cross-sectional view of the lid of FIG. 6A in the expanded state and including the tortuous path filter disposed therein according to one or more embodiments shown and described herein.

Referring now to FIGS. 6C-6D, the modular filter lid assembly 430 includes a pair of filter structures 120, 140 disposed within the modular body 431, and in particular between the exterior surface 432 and the interior surface 434. More specifically, the modular filter lid assembly 430 includes the exterior filter structure 120 disposed within the modular body 431 and positioned along a lower interior surface 438 of the modular filter lid assembly 430. Further, the modular filter lid assembly 430 includes the interior filter structure 140 disposed within the modular body 431 and positioned along the interior surface 134 of the modular filter lid assembly 430. It should be understood that the filter structures 120, 140 are substantially similar to the filter structures 120, 140 shown and described above such that each of the filter structures 120, 140 of the modular filter lid assembly 430 includes a plurality of ridges 122, 142 and a plurality of troughs 124, 144, respectively, as similarly described and shown above with respect to the filter structures 120, 140 of the filter assembly 130. In this instance, the pair of filter structures 120, 140, of the modular filter lid assembly 430 form a tortuous path filter within the modular body 431 that is configured to mesh with one another between the exterior surface 432 and the interior surface 434 of the modular filter lid assembly 430.

Referring specifically to FIG. 6C, the modular filter lid assembly 430 is schematically depicted in the first, compacted state such that the pair of filter structures 120, 140 are positioned in a first configuration with the pair of opposing ends 436 separated from one another by a first distance. In this instance, a longitudinal length of the tortuous path filter formed by the filter structures 120, 140 is defined between the inlet 437 and the outlet opening 118 with the plurality of ridges 122, 142 and the plurality of troughs 124, 144 positioned therebetween. As will be described in greater detail herein, the tortuous path filter formed by the filter structures 120, 140 is configured to include additional ridges 122, 142 and troughs 124, 144 extending between the inlet 437 and the outlet opening 118 when in the second configuration relative to the first configuration shown and described herein.

Referring now to FIG. 6D, the modular filter lid assembly 430 is schematically depicted in the second, expanded state such that the pair of filter structures 120, 140 are positioned in a second configuration with the pair of opposing ends 436 separated from one another by a second distance that is greater than the first distance. In this instance, a longitudinal length of the tortuous path filter formed by the filter structures 120, 140 is defined between the inlet 437 and the outlet opening 118 in the +/−X axis of FIG. 6D with the plurality of ridges 122, 142 and the plurality of troughs 124, 144 positioned therebetween. The tortuous path filter includes additional ridges 122, 142 and troughs 124, 144 extending between the inlet 437 and the outlet opening 118 in the second configuration relative to the first configuration in response to actuation of the plurality of movable body segments 433, and a separation of the pair of opposing ends 436 from one another (i.e. in the +/−X direction of the coordinate axes in the figures). It should be understood that with the inlet 437 positioned along at least one of the pair of opposing ends 436, a size and/or shape of the inlet 437 remains fixed in the second, expanded state of the modular body 431 relative to the first, compacted state.

In some embodiments, the plurality of ridges 122, 142 of the filter structures 120, 140 are structurally configured to be slidably received within one another when in the first configuration. In other embodiments, the plurality of ridges 122, 142 and the plurality of troughs 124, 144 of the filter structures 120, 140 may be individually foldable when in the first configuration. Still in other embodiments the plurality of ridges 122, 142 may formed of flexibly depressible materials such that the plurality of ridges 122, 142 are selectively depressed when in the first configuration. In either instance, the filter structures 120, 140 are configured to be modularly adjustable to increase and/or decrease a quantity of the plurality of ridges 122, 142 and the plurality of troughs 124, 144 included therein in response to an expansion and/or collapse of the modular body 431 as a longitudinal length defined between the pair of opposing ends 436 is adjusted in the +/−X direction of FIGS. 6C-6D. In other embodiments, the modular filter lid assembly 430 may be configured to selectively expand and/or collapse in various other configurations, shapes, sizes, orientations, and/or the like without departing from the scope of the present disclosure. For example, a lateral width of the modular body 431 defined between the pair of sidewalls 435 may be selectively adjustable (i.e. in the +/−Y direction of the coordinate axes in the figures) in addition to and/or in lieu of a longitudinal length of the modular body 431 defined between the pair of opposing ends 436.

V. Alternative Modular Lid with Rectangular Tortuous Path Filter

Figure 7B:
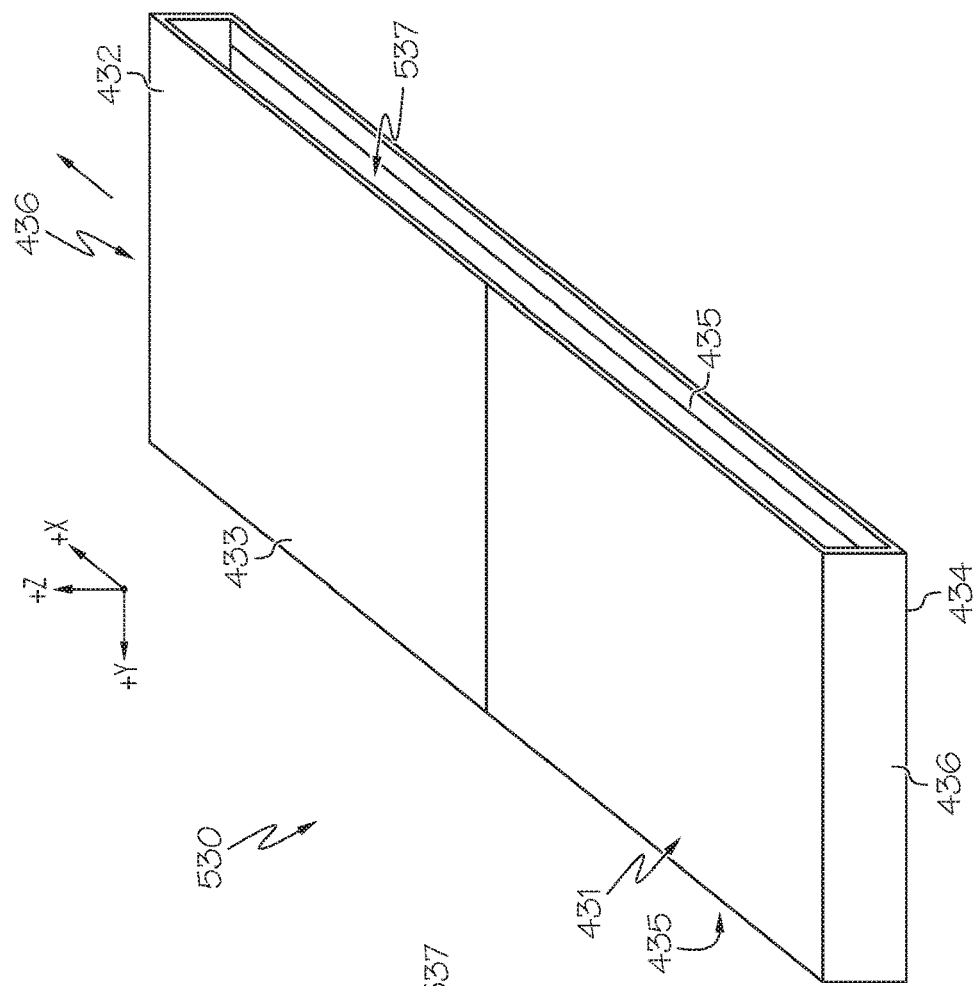
FIG. 7B is a perspective view of the lid of FIG. 7A, with the lid in an expanded state according to one or more embodiments shown and described herein.
Figure 7A:
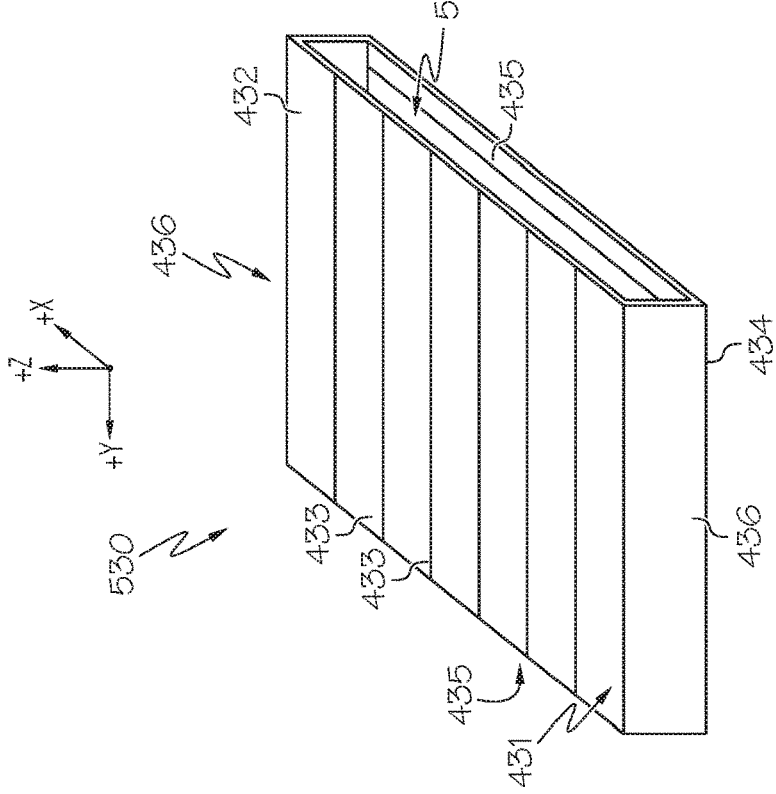
FIG. 7A is a perspective view of another exemplary lid for a sterilization container, with the lid in a compact state according to one or more embodiments shown and described herein.

Referring now to FIGS. 7A-7B, an alternative embodiment of a modular filter lid assembly 530 that is substantially similar to the modular filter lid assembly 430 shown and described above is schematically depicted. Except as otherwise described below, the modular filter lid assembly 530 may be configured and operable like the modular filter lid assembly 430 such that like reference numerals are used to identify like components. It should be understood that the modular filter lid assembly 530 of the present example may be readily incorporated into the sterilization containers 100, 200, 300 described above, and more particularly the modular filter lid assembly 530 may be readily utilized with the lids 110, 210, 310 shown and described above. In many respects, the modular filter lid assembly 530 functions substantially similar to the modular filter lid assembly 430 except as otherwise described herein.

Referring specifically to FIG. 7A, the modular body 431 of the modular filter lid assembly 530 is defined by the exterior surface 432, the interior surface 434, the pair of sidewalls 435 and the pair of opposing ends 436. The modular body 431 includes a lateral width extending between the pair of sidewalls 435 (i.e. in the +/−Y direction of the coordinate axes in the figures) and a longitudinal length extending between the pair of opposing ends 436 (i.e. in the +/−X direction of the coordinate axes in the figures). Similar to the modular filter lid assembly 430 shown and described above, the modular body 431 of the modular filter lid assembly 530 is formed of the plurality of movable body segments 433 positioned between the pair of opposing ends 436. Each of the plurality of movable body segments 433 of the modular body 431 is configured to extend outwardly relative to one another to selectively form a plurality of configurations, shapes, profiles, orientations and/or the like of the modular filter lid assembly 530. In other words, the plurality of movable body segments 433 are modular such that each of the movable body segments 433 are selectively expandable and/or collapsible relative to one another.

At least one of the pair of sidewalls 435 of the modular body 431 includes an inlet 537 formed therein. The inlet 537 extends into the modular body 431 of the modular filter lid assembly 530 and is configured to facilitate access to a tortuous path filter of the modular filter lid assembly 530 disposed within the modular body 431. The modular body 431 of the modular filter lid assembly 530 is depicted in a first, compacted state with the pair of opposing ends 436 separated from one another by a first distance. In this instance, the tortuous path filter formed within the modular body 431 has a first configuration based on the first, compacted state of the modular body 431. It should be understood that the modular filter lid assembly 530 may include a tortuous path filter within the modular body 431 similar to the modular filter lid assembly 430 shown and described above (see FIGS. 6C-6D).

Referring now to FIG. 7B, the modular body 431 of the modular filter lid assembly 530 is depicted in a second, expanded state with the pair of opposing ends 436 separated from one another by a second distance that is larger than the first distance shown and described above. In this instance, the tortuous path filter formed within the modular body 431 has a second configuration based on the second, expanded state of the modular body 431. With the modular body 431 formed of a plurality of movable body segments 433, the modular body 431 of the modular filter lid assembly 530 is configured to selectively transition between the first, compacted state and the second, expanded state in response to an outward expansion of each of the plurality of movable body segments 433.

For example, the pair of opposing ends 436 of the modular body 431 may be physically manipulated to manually adjust (i.e. increase and/or decrease) a separation distance therebetween, thereby modifying a longitudinal length of the modular body 431 in the +/−X direction of FIGS. 7A-7B. It should be understood that with the inlet 537 positioned along at least one of the pair of sidewalls ends 535, a size and/or shape of the inlet 537 is modularly adjustable simultaneously with the modular body 431 of the modular filter lid assembly 530. In particular, the inlet 537 is configured to expand along the sidewall 435 as the modular body 431 transitions from the first, compacted state to the second, expanded state.

It should be understood that the plurality of movable body segments 433 of the modular body 431 may be configured to transition from the first, compacted state to the second, expanded state in various suitable manners as described above with respect to modular filter lid assembly 430 without departing from the scope of the present disclosure. It should further be understood that the modular filter lid assembly 530 includes a pair of modular filter structures disposed within the modular body 431 between the exterior surface 432 and the interior surface 434 forming a tortuous path filter therein. The tortuous path filter of the modular filter lid assembly 530 is configured to selectively expand and/or collapse simultaneously with a corresponding expansion and/or collapse of the plurality of movable body segments 433 of the modular body 431. In other embodiments, the modular filter lid assembly 530 may be configured to selectively expand and/or collapse in various other configurations, shapes, sizes, orientations, and/or the like without departing from the scope of the present disclosure. For example, a lateral width of the modular body 431 defined between the pair of sidewalls 435 may be selectively adjustable (i.e. in the +/−Y direction of the coordinate axes in the figures) in addition to and/or in lieu of a longitudinal length of the modular body 431 defined between the pair of opposing ends 436 (i.e. in the +/−X direction of the coordinate axes in the figures).

VI. Alternative Sterilization Container with Vertical Tortuous Path Filter

Figure 8:
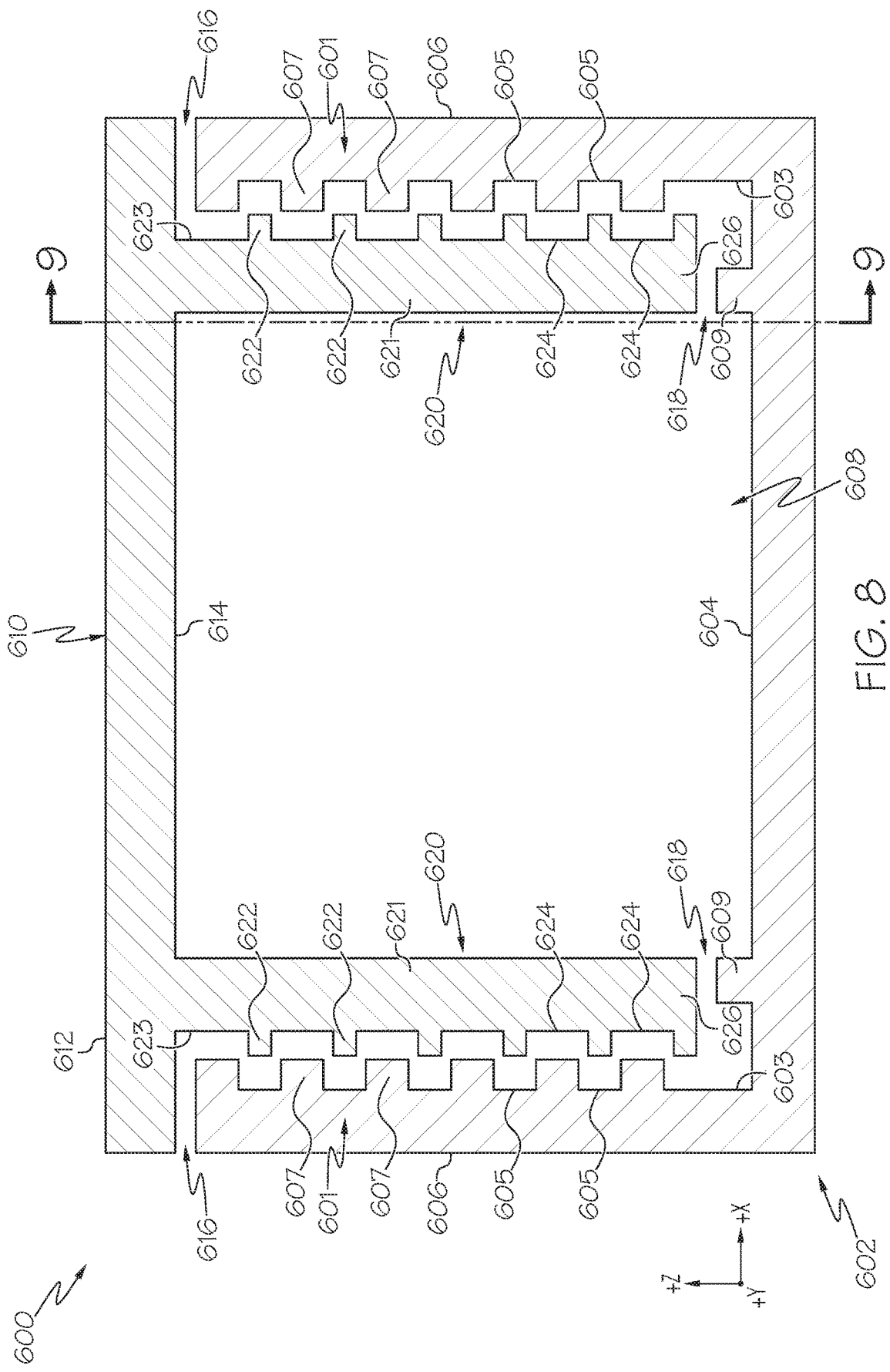
FIG. 8 is a side cross-sectional view another exemplary sterilization container including a body and lid forming a tortuous path filter along corresponding sidewalls according to one or more embodiments shown and described herein.

FIGS. 8-9 schematically depict an alternative embodiment of a sterilization container 600 that is substantially similar to the sterilization containers 100, 200, 300 shown and described above. Except as otherwise described below, the sterilization container 600 may be configured and operable like the sterilization containers 100, 200, 300. For instance, the sterilization container 600 includes a body 602 formed by a bottom wall 604 and a plurality of sidewalls 606 thereby defining an interior volume 608 therein. The sterilization container 600 includes a lid 610 that is secured to the body 602 and includes an exterior surface 612 and an interior surface 614 opposite of the exterior surface 612. The lid 210 may include a plurality of sidewalls 621 that extend outwardly from the interior surface 614 that are sized and shaped to be received within the interior volume 608 of the body 602. It should be understood that the lid 610 includes a corresponding quantity of sidewalls 621 relative to the plurality of sidewalls 606 of the body 602. Additionally, the interior volume 608 of the body 602 is generally sized to receive one or more devices therein, such as, for example, medical apparatuses, instruments, and/or the like.

Referring specifically to FIG. 8, in some embodiments each of the sidewalls 606 of the body 602 includes a filter structure 601 disposed thereon and positioned along an interior surface 603 of the sidewall 606 that is positioned inwardly into the interior volume 608. Each of the filter structures 601 of the plurality of sidewalls 606 includes a plurality of ridges 607 extending laterally outward along the interior surface 603 and a plurality of troughs 605 formed along the interior surface 603 and positioned in between a pair of adjacent ridges 607. It should be understood that the plurality of ridges 607 and the plurality of troughs 605 may be configured and operable similar to the plurality of ridges 122, 142 and the plurality of troughs 124, 144 shown and described in greater detail above.

In embodiments, each of the sidewalls 621 of the lid 610 includes a filter structure 620 disposed thereon positioned along an exterior surface 623 of the sidewall 621 that is positioned outwardly. Each of the filter structures 620 of the plurality of sidewalls 621 includes a plurality of ridges 622 extending laterally outward along the exterior surface 623 and a plurality of troughs 624 formed along the exterior surface 623 and positioned in between a pair of adjacent ridges 622. It should be understood that the plurality of ridges 622 and the plurality of troughs 624 may be configured and operable similar to the plurality of ridges 122, 142 and the plurality of troughs 124, 144 shown and described in greater detail above. It should be further understood that in some embodiments a subset of the plurality of sidewalls 621 of the lid 610 includes the filter structure 620 disposed thereon. In this instance, a corresponding subset of the plurality of sidewalls 606 of the body 602 include the filter structure 601 disposed thereon.

Still referring to FIG. 8, the body 602 of the sterilization container 600 further includes one or more standoffs 609 extending outwardly from the bottom wall 604 and into the interior volume 608 at a predetermined length. As described in greater detail herein, the one or more standoffs 609 of the body 602 are sized, shaped, and configured to form a gap proximate to the bottom wall 604 to serve as an outlet opening for a tortuous path filter formed in the sterilization container 600 in response to the body 602 coupling the lid 610. In some embodiments, the body 602 includes a single standoff 609 extending continuously about a perimeter of the bottom wall 604 adjacent to each of the plurality of sidewalls 606. In other embodiments, the body 602 includes a plurality of standoffs 609 extending about the bottom wall 604 adjacent to each of the plurality of sidewalls 606. Various other arrangements and/or quantities of the one or more standoffs 609 may be included in the sterilization container 600 without departing from the scope of the present disclosure.

It should be understood that the one or more standoffs 609 of the body 602 are positioned adjacent to each of the sidewalls 606 by a predetermined distance. As described in greater detail herein, the one or more standoffs 609 are positioned along the bottom wall 604 of the body 602 in alignment with a location of the plurality of sidewalls 621 of the lid 610 in response to the lid 610 being received over the body 602. The lid 610 of the sterilization container 600 further includes one or more standoffs 626 extending outwardly from the each of the plurality of sidewalls 621 at a predetermined length. As will be described in greater detail herein, in some embodiments the lid 610 includes a single standoff 626 extending continuously about an end of the plurality of sidewalls 621 opposite of the interior surface 614.

Still referring to FIG. 8, in other embodiments the lid 610 includes a plurality of standoffs 626 extending about an end of each of the plurality of sidewalls 621. Various other arrangements and/or quantities of the one or more standoffs 626 may be included in the sterilization container 600 without departing from the scope of the present disclosure. As described in greater detail herein, the one or more standoffs 626 are positioned along an end of the plurality of sidewalls 621 in alignment with a location of the one or more standoffs 609 along the bottom wall 604 in response to the lid 610 being received over the body 602. Although not shown, it should be understood that the body 602 and/or the lid 610 of the sterilization container 600 may further include one or more latch elements for securely fastening the body 602 and the lid 610 to one another.

With the lid 610 disposed over the body 602 of the sterilization container 600, the plurality of sidewalls 621 are received within the interior volume 608 and positioned adjacent to the plurality of sidewalls 606. In particular, the exterior surface 623 of the plurality of sidewalls 621 are positioned proximate to and extending toward the interior surface 603 of the plurality of sidewalls 606 when the lid 610 is received in the body 602. With the filter structure 620 of the plurality of sidewalls 621 positioned along the exterior surface 623 and the filter structure 601 of the plurality of sidewalls 606 positioned along the interior surface 603, a tortuous path filter is formed between the plurality of sidewalls 606, 621. More specifically, the plurality of ridges 607 and the plurality of troughs 605 of the filter structure 601 are configured to mesh with the plurality of ridges 622 and the plurality of troughs 624 thereby forming a tortuous path filter between the lid 610 and the body 602.

Still referring to FIG. 8, a plurality of inlets 616 and a plurality of outlet openings 618 are formed between the lid 610 and the body 602 in response to the lid 610 being positioned over the body 602 and the plurality of sidewalls 621 being received within the interior volume 608. In particular, the plurality of inlets 616 are formed between the interior surface 614, the plurality of sidewalls 621, and the plurality of sidewalls 606. The plurality of outlet openings 618 are formed between the standoff 609 of the bottom wall 604, the standoff 626 of the plurality of sidewalls 621, and the plurality of sidewalls 606. It should be understood that the lid 610 and/or the body 602 is sized, shaped and configured to form the inlet 616 and the outlet opening 618 when securely coupled to one another. In other words, the inlet 616 and the outlet opening 618 comprise a gap formed between the lid 610 and the body 602 in response to the lid 610 and the body 602 securely engaging one another.

It should be understood that the plurality of inlets 616 and/or the plurality of outlet openings 618 may include various sizes, shapes, and/or positions than those shown and described herein without departing from the scope of the present disclosure. Additionally, it should be understood the plurality of inlets 616 and the plurality of outlet openings 618 are located proximate to the plurality of sidewalls 606, 621 that include the filter structures 601, 620 disposed thereon. Accordingly, in embodiments with only a subset of the plurality of sidewalls 606, 621 including the filter structures 601, 620, respectively, a gap formed by the inlet 616 and the outlet opening 618 is omitted between the lid 610 and the body 602 along the plurality of sidewalls 606, 621 not including the filter structures 601, 620. In some embodiments, the filter structures 601, 620 are further configured to form a gasket between the lid 610 and the body 602.

Figure 9A:
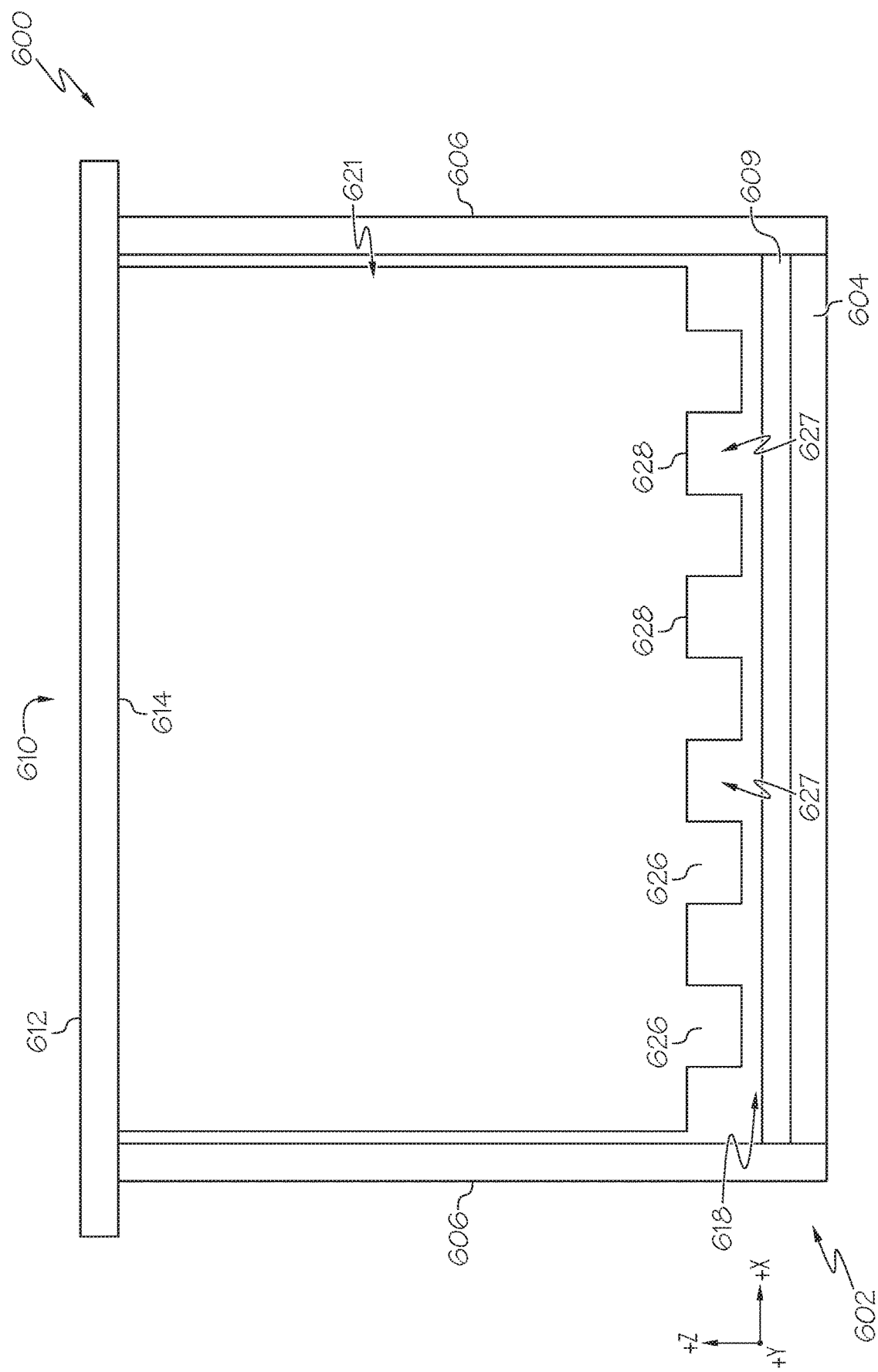
FIG. 9A is a side cross-sectional view of the sterilization container of FIG. 8 according to one or more embodiments shown and described herein.

Referring now to FIG. 9A, the sidewall 621 of the lid 610 is schematically depicted including the one or more standoffs 626 described and shown above. In the embodiment, the sidewall 621 of the lid 610 includes a plurality of standoffs 626 disposed along a bottom end of the sidewall 621. In particular, each of the plurality of standoff 626 of the sidewall 621 is separated from one another by a gap 627 formed therebetween thereby defining a plurality of recessed standoffs 628 at the gaps 627. The plurality of recessed standoffs 628 are positioned distally from the standoff 609 of the body 602 along the bottom wall 604 relative to the plurality of standoffs 626. In this instance, the outlet opening 618 formed between the standoff 609 of the body 602 and the standoff 626 of the sidewall 621 is increased along the plurality of recessed standoffs 628 with the gaps 627 formed therein. It should be understood that in other embodiments the standoff 626 of the sidewall 621 may extend uniformly along a bottom end of the sidewall 621 such that the plurality of recessed standoffs 628 and the plurality of gaps 627 are omitted entirely from the sterilization container 600.

For example, referring now to FIG. 9B, an alternative sterilization container 600' is schematically depicted that is substantially similar to the sterilization container 600 shown and described above except for the differences explicitly noted herein. Therefore, identical or substantially similar components are marked with the same reference numerals without further discussion. It should be understood that any components and operabilities of the sterilization container 600' that are not described explicitly below may be the same as the components and operabilities of the sterilization container 600 described above. In particular, the lid 610 of the sterilization container 600' includes a plurality of sidewalls 621' including a standoff 626' extending along a bottom end of the sidewall 621'. In this instance, the standoff 626' forms a uniform, planar end of the sidewall 621' of the lid 610.

The body 602 of the sterilization container 600' includes one or more standoffs 609' extending outwardly from the bottom wall 604 and toward the plurality of sidewalls 621' of the lid 610. In particular, the bottom wall 604 of the body 602 includes a plurality of standoffs 609' such that each of the plurality of standoff 609' along the bottom wall 604 is separated from one another by a gap 618' formed therebetween. In this instance, the outlet opening 618 formed between the plurality of standoffs 609' of the body 602 and the standoff 626' of the plurality of sidewalls 621' is increased along the plurality of gaps 618' formed therebetween. It should be understood that in other embodiments both the standoff 626, 626' of the plurality of sidewalls 621, 621' and the standoff 609, 609' of the body 602 may include various other shapes, sizes, and/or configurations than those shown and described herein to form varying outlet openings 118 between the lid 610 and the body 602 of the sterilization container 600, 600' without departing from the scope of the present disclosure.

VII. Alternative Sterilization Container with Radial Tortuous Path Filter

Figure 10:
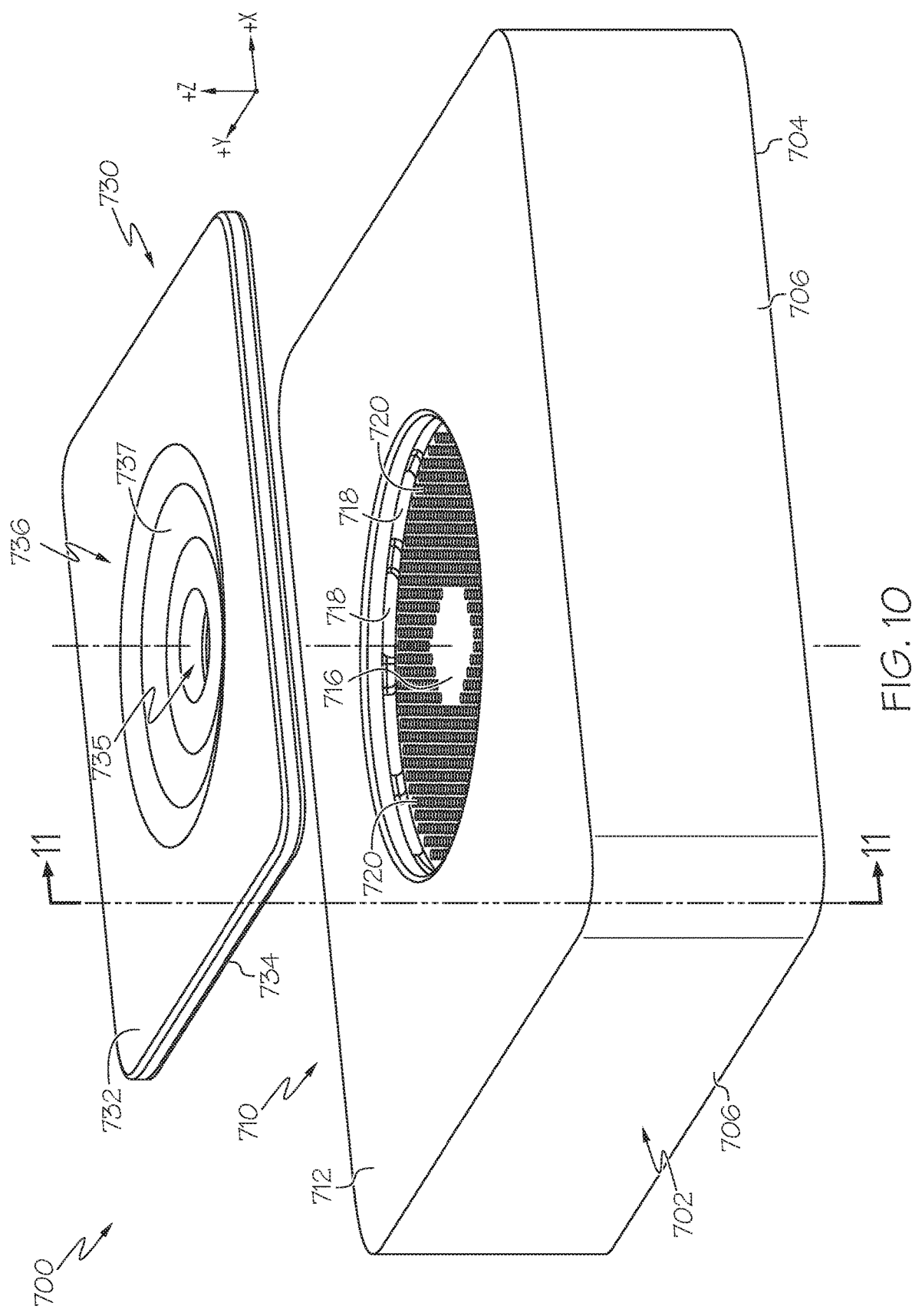
FIG. 10 is a perspective view of another exemplary sterilization container including a lid and a filter assembly according to one or more embodiments shown and described herein.
Figure 11:
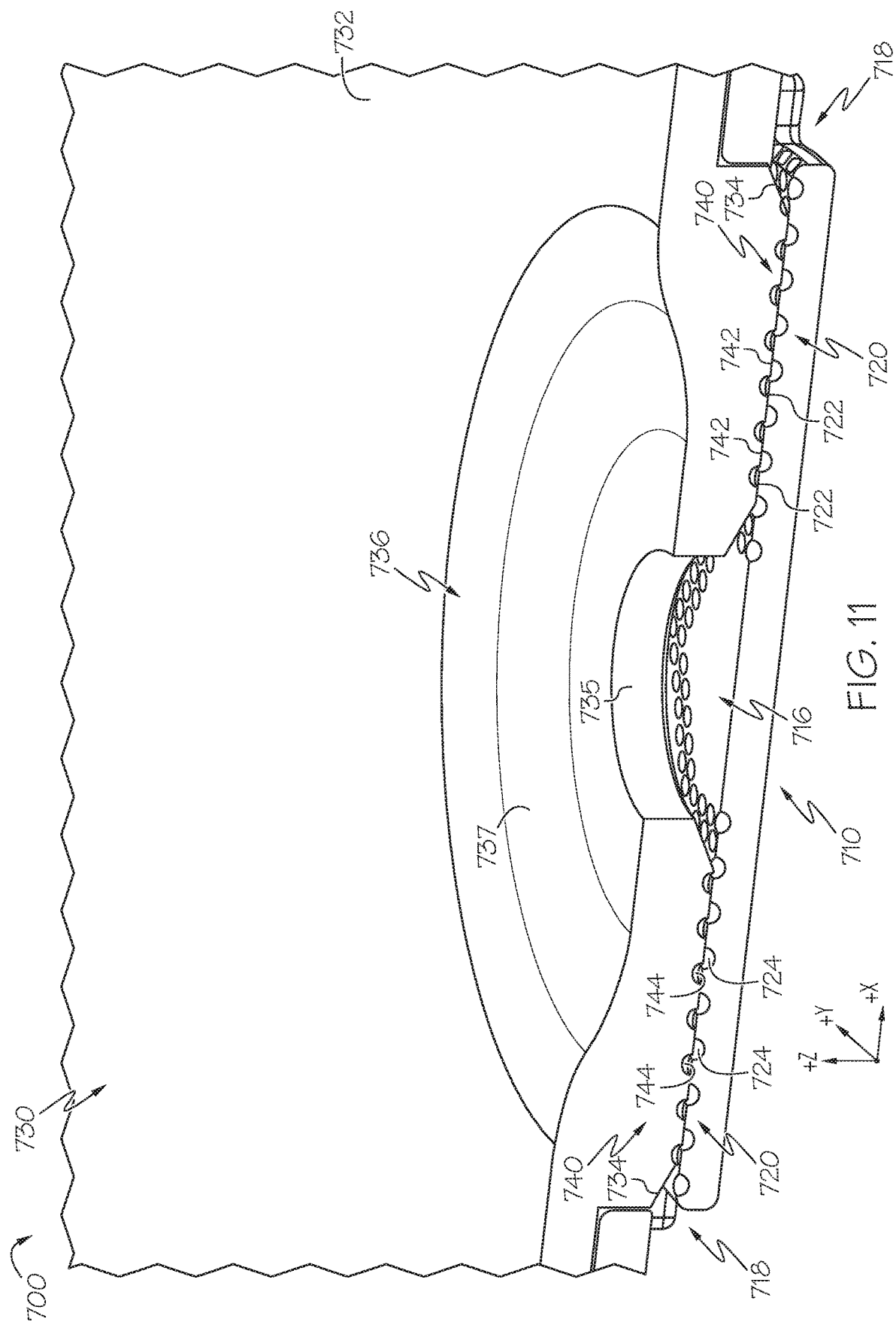
FIG. 11 is a cross-sectional view of the sterilization container of FIG. 10 with the lid and filter assembly forming a tortuous path filter according to one or more embodiments shown and described herein.
Figure 12:
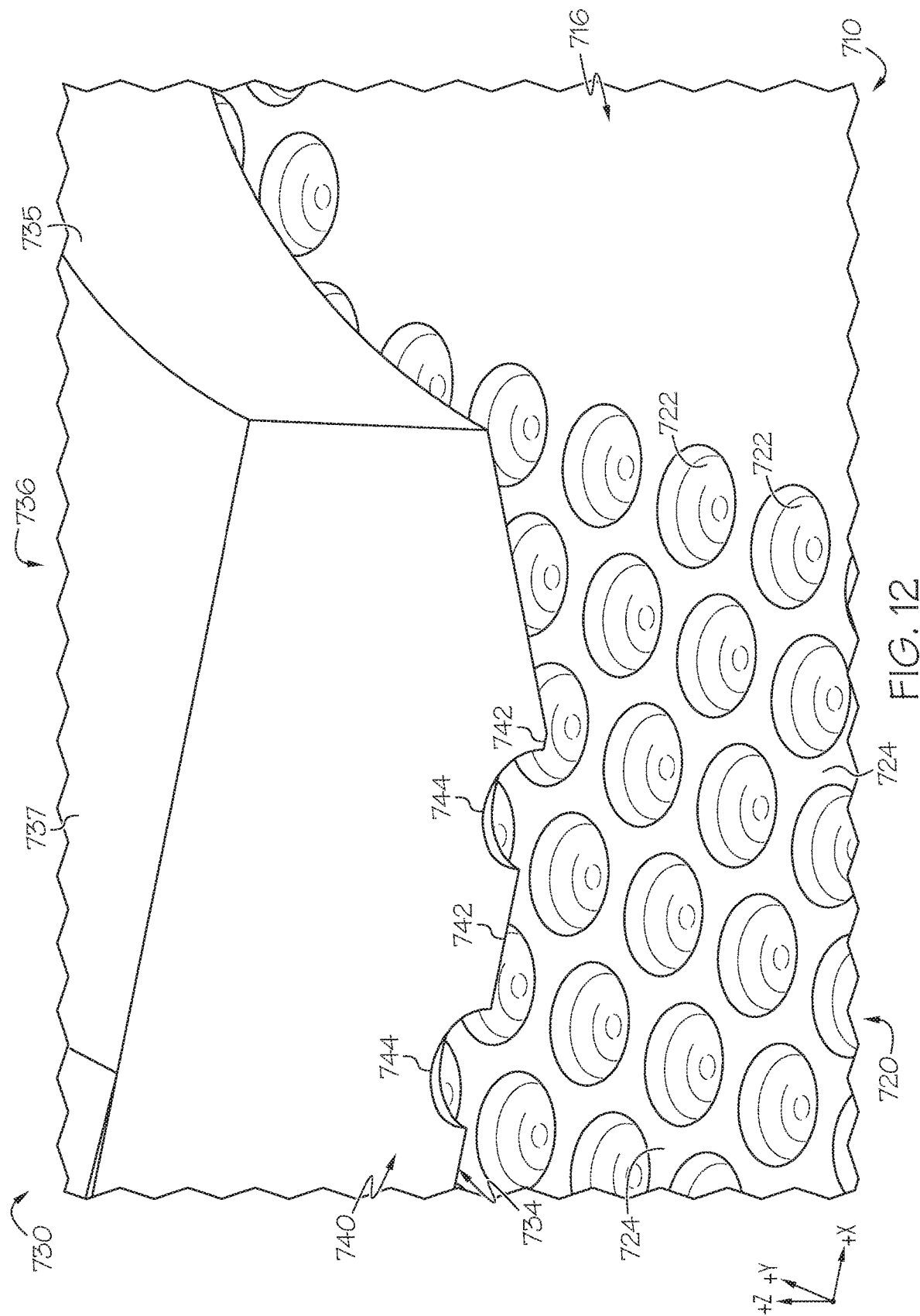
FIG. 12 is a partial cross-sectional view of the sterilization container of FIG. 10 with the lid and filter assembly including a plurality of dimples according to one or more embodiments shown and described herein.

FIGS. 10-12 schematically depict an alternative embodiment of a sterilization container 700 that is substantially similar to the sterilization containers 100, 200, 300 shown and described above. Except as otherwise described below, the sterilization container 700 may be configured and operable like the sterilization containers 100, 200, 300. Referring specifically to FIG. 10, the sterilization container 700 includes a body 702 formed by a bottom wall 204 and a plurality of sidewalls 706 defining an interior volume therein. The sterilization container 700 includes a lid 710 that is secured to the body 702 and includes an exterior surface 712 and an interior surface opposite of the exterior surface 712. The exterior surface 712 of the lid 710 includes a recessed inlet 716, and a plurality of outlet openings 718 disposed thereon. It should be understood that in some embodiments the lid 110 may include one or more latch elements similar to the latch elements 111 of the lid 110 described and shown above that are sized, shaped and configured to securely couple the lid 710 to one or more other components of the sterilization container 700, such as a filter assembly 730. Additionally, the interior volume of the body 702 is generally sized to receive one or more devices therein, such as, for example, medical apparatuses, instruments, and/or the like.

The exterior surface 712 of the lid 710 further includes a radial filter structure 720 disposed about the recessed inlet 716, wherein the filter structure 720 extends along the exterior surface 712 and is positioned between the recessed inlet 716 and the plurality of outlet openings 718. In the embodiment, the filter structure 720 includes a circular shape, profile, and/or configuration. The recessed inlet 716 forms a depressed surface along the exterior surface 712 of the lid 710 and is disposed within the filter structure 720 and the plurality of outlet openings 718. It should be understood that the depressed surface formed by the recessed inlet 716 is relative to a planar surface of the exterior surface 712. The plurality of outlet openings 718 of the lid 710 is positioned in an annular array about the filter structure 720 and the recessed inlet 716, and more specifically the plurality of outlet openings 718 are positioned adjacent to a terminal boundary of the filter structure 720 opposite of the recessed inlet 716. In other embodiments, the lid 710 may include filter structures with various other suitable shapes, sizes, and/or configurations, such as, for example, a rectangular filter structure.

Still referring to FIG. 10, the sterilization container 700 further includes a filter assembly 730 having an exterior surface 732 and an interior surface 734 positioned opposite of the exterior surface 732. The exterior surface 732 of the filter assembly 730 includes a radial inlet 736 disposed thereon, and in particular the radial inlet 736 includes a radial inlet opening 735 and a radial ramp 737 disposed about the radial inlet opening 735. In the embodiment, a diameter of the radial inlet opening 735 is sized and shaped in accordance with a size and shape of the recessed inlet 716, and a size and shape of the radial inlet 736 is sized and shaped in accordance with a size and shape of the radial filter structure 720. Accordingly, a radially-shaped opening is formed through the filter assembly 730 at the radial inlet 736. The radial ramp 737 of the filter assembly 730 is configured to form a curved surface between the exterior surface 732 and the radial inlet opening 735.

It should be understood that in other embodiments the filter assembly 730 may include a larger and/or smaller radial inlet 736 than those shown and described herein without departing from the scope of the present disclosure. The radial ramp 737 is configured to direct airflow and/or other materials, substances, and/or the like toward the radial inlet opening 735. It should be understood that in other embodiments the radial inlet opening 735 and/or the radial ramp 737 of the radial inlet 736 may have various other sizes and/or shapes than those shown and described herein. Although not shown, it should be understood that in some embodiments the filter assembly 730 of the sterilization container 700 may further include one or more latch elements disposed on the interior surface 734 of the filter assembly 730 for securely coupling the filter assembly 730 to the lid 710. Except as otherwise described below, it should be understood that the latch elements of the filter assembly 730 are substantially similar and configured like the latch element 131 of the filter assembly 730 shown and described above.

Referring now to FIG. 11, the sterilization container 700 is schematically depicted with the filter assembly 730 received on and coupled to the lid 710 such that the radial inlet 736 is disposed over the recessed inlet 716. In the embodiment, the radial filter structure 720 of the lid 710 includes a plurality of ledges 722 and a plurality of dimples 724, and the filter assembly 730 includes a radial filter structure 740 disposed along the interior surface 734. In particular, the radial filter structure 740 includes a plurality of ledges 742 and a plurality of dimples 744 positioned along the interior surface 734. Each ledge 722, 742 of the plurality of ledges 722, 742 is formed between a pair of adjacent dimples 724, 744 of the plurality of dimples 724, 744, respectively, such that a size and shape of each of the ledges 722, 742 is relative to a distance and/or depth between each of the pair of adjacent dimples 724, 744 of the respective filter structures 720, 740.

In some embodiments, the distance between adjacent ledges 722, 742 of the filter structure 720, 740 varies relative to one another along the lid 710 and/or the filter assembly 730, respectively. In other embodiments, the distance between adjacent ledges 722, 742 of the filter structure 720, 740, respectively, may be substantially similar to one another. Securing the interior surface 734 of the filter assembly 730 onto the exterior surface 712 of the lid 710 via engagement of corresponding latch elements of the lid 710 and the filter assembly 730, respectively, provides a coupling of the filter structure 720 of the lid 710 with the filter structure 740 of the filter assembly 730. In this instance, a tortuous filter path formed between the lid 710 and the filter assembly 730, and in particular a radial tortuous filter path due a radially-shaped profile of the filter structures 720, 740 of the lid 710 and the filter assembly 730.

Still referring to FIG. 11, the sterilization container 700 includes a single ingress point into the radial tortuous filter paths formed by the filter structure 720 of the lid 710 and the filter structure 740 of the filter assembly 730 at the radial inlet opening 735 and the recessed inlet 716, respectively. Additionally, the sterilization container 700 includes multiple egress points from the radial tortuous path filter via the plurality of outlet openings 718 of the lid 710. It should be understood that the plurality of ledges 722, 742 of the filter structures 720, 740 are sized and shaped to generate a plurality of structural impediments between the lid 710 and the filter assembly 730 in the form of physical obstructions, barriers, hurdles and/or the like along a tortuous filter path formed between the filter structures 720, 740, respectively. The plurality of structural impediments formed by the plurality of ledges 722, 742 may vary based on a predetermined size and shape of the ledges 722, 742, such as, for example, a length, width and/or position of each of the plurality of ledges 722, 742.

Referring now to FIG. 12, the plurality of dimples 724, 744 formed between the plurality of ledges 722, 742 of the filter structures 720, 740 are sized and shaped to generate a plurality of structural impediments between the lid 710 and the filter assembly 730 in the form of physical cavities, recesses, depressions, troughs, and/or the like along the radial tortuous filter path formed between the filter structures 720, 740, respectively. The plurality of structural impediments formed by the plurality of dimples 724, 744 may vary based on a predetermined size and shape of the dimples 724, 744 such as, for example, a depth, diameter and/or position of each of the plurality of dimples 724, 744. With the lid 710 secured to the body 702 and the filter assembly 730 positioned over the lid 710, the filter structure 740 is disposed over the filter structure 720 thereby forming a tortuous filter path therebetween.

In other words, the filter structure 720 is configured to mesh with the filter structure 740 in response to the lid 710 receiving the filter assembly 730 thereon. In particular, the plurality of ledges 722 of the filter structure 720 extend at least partially over the plurality of ledges 742 and/or the plurality of dimples 744 of the filter structure 740. Further, the plurality of ledges 742 of the filter structure 740 extends at least partially over the plurality of ledges 722 and/or the plurality of dimples 724 of the filter structure 720. It should be understood that in some embodiments the plurality of ledges 722, 742 of the filter structures 720, 740 are at least partially inserted into the plurality of dimples 724, 744 when the filter structure 740 is disposed over the filter structure 720 such that the plurality of dimples 724, 744 are sized and shaped to at least partially receive the plurality of ledges 722, 742 therein. In other embodiments, the plurality of ledges 722, 742 of the filter structures 720, 740 are configured to engage one another such that the plurality of ledges 722 at least partially abut against the plurality of ledges 742 of the filter structure 740.

VIII. Stackable Sterilization Containers with Nesting Feature

Figure 13:
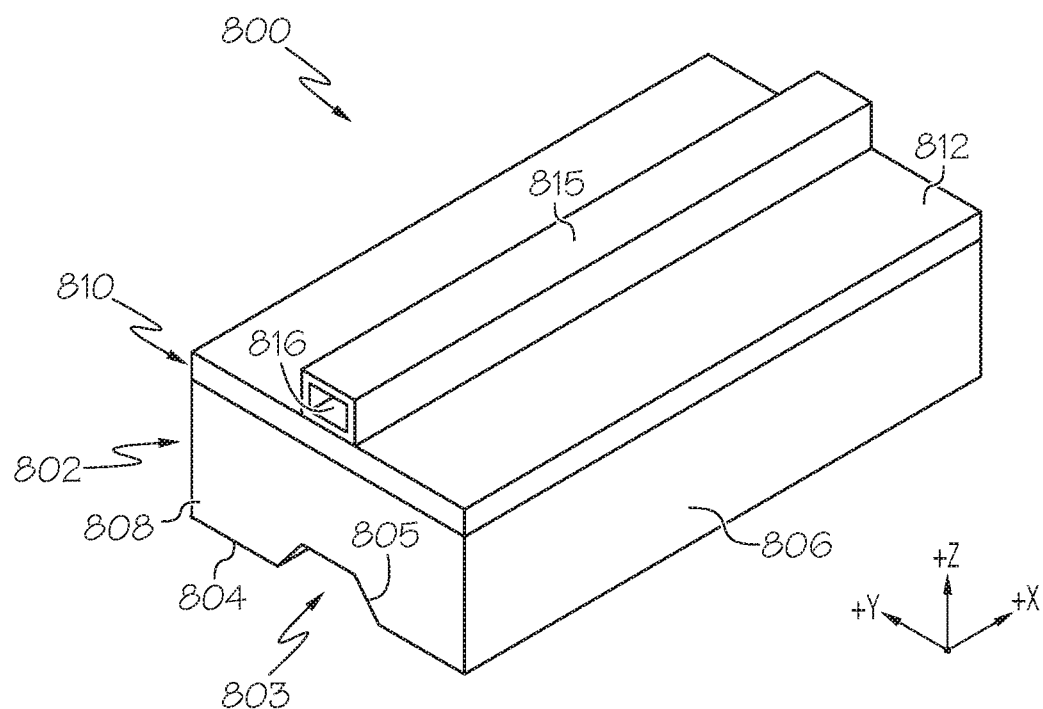
FIG. 13 is a perspective view of another exemplary sterilization container including a body, a lid, and a filter assembly having a nesting feature according to one or more embodiments shown and described herein.
Figure 14:
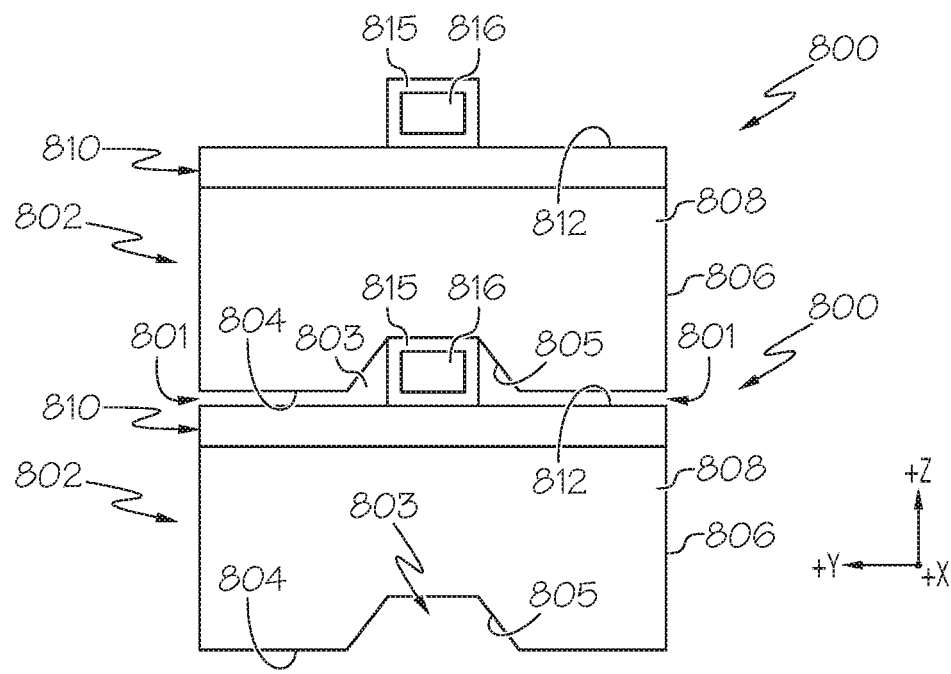
FIG. 14 is a side view of a pair of the sterilization containers of FIG. 13 stacked atop one another according to one or more embodiments shown and described herein.

FIGS. 13-14 schematically depict an alternative embodiment of a sterilization container 800. It should be understood that the sterilization container 800 may be substantially similar to the sterilization containers 100, 200, 300, 600, 700 shown and described above. Except as otherwise described below, the sterilization container 800 may be configured and operable like the sterilization containers 100, 200, 300, 600, 700. Referring specifically to FIG. 13, the sterilization container 800 includes a body 802 formed by a bottom wall 804, one or more sidewalls 806, and one or more end walls 808. The walls 804, 806, 808 of the body 802 are generally sized and shaped to form an interior volume that is configured to receive one or more devices therein, such as, for example, medical apparatuses, instruments, and/or the like. The body 802 of the sterilization container 800 further includes one or more engagement surfaces 805 along a juncture between the bottom wall 804 and the one or more end walls 808 thereby forming one or more recessed channels 803 extending therethrough. The one or more engagement surfaces 805 positioned between the bottom wall 804 and the end walls 808 extend at varying angles, orientations, and/or configurations therethrough to form the recessed channel 803 of the body 802. As described in detail herein, the one or more recessed channels 803 provide nesting features for coupling the body 802 to one or more other components of the sterilization container 800, such as, for example, a lid 810.

In the present example, the body 802 of the sterilization container 800 includes a pair of opposing end walls 808 defining a longitudinal length of the body 802 in the +/−X direction of FIG. 13, and a pair of opposing sidewalls 806 defining a lateral width of the body 802 in the +/−Y direction of FIG. 13. The pair of opposing end walls 808 of the body 802 includes a plurality of engagement surfaces 805 extending from the bottom wall 804 and along each of the end walls 808, thereby defining at least one recessed channel 803 thereon. In the present example the at least one recessed channel 803 extends along a longitudinal length of the bottom wall 804 of the body 802 between the pair of end walls 808 (i.e. in the +/−X direction of the coordinate axes in the figures) and has a trapezoidal configuration. As described in greater detail herein, the engagement surfaces 805 of the body 802 are sized and shaped in accordance with a size and shape of a component of the sterilization container 800, such as, for example, a lid 810. It should be understood that in other embodiments the body 802 of the sterilization container 800 may include additional and/or fewer engagement surfaces 805 at a juncture between the bottom wall 804 and the end walls 808 than those shown and described herein without departing from the scope of the present disclosure. Additionally, in some embodiments the engagement surfaces 805 of the body 802 may include various other sizes, shapes, arrangements, and/or configurations to thereby form recessed channels with varying profiles.

Still referring to FIG. 13, the sterilization container 800 further includes a lid 810 defined by an exterior surface 812 and an interior surface opposite of the exterior surface 812. The lid 810 of the sterilization container 800 further includes at least one coupling mechanism 815 disposed along the exterior surface 812. In particular, the coupling mechanism 815 of the lid 810 extends outwardly from the exterior surface 812 such that the coupling mechanism 815 forms a protrusion thereon. The coupling mechanism 815 of the lid 810 extends along a longitudinal length of the exterior surface 812 in the +/−X direction of FIG. 13 and is sized and shaped in accordance with a configuration of the recessed channel 803 of the body 802. As described in greater detail herein, the coupling mechanism 815 provides a nesting feature for coupling the lid 810 to one or more other components of the sterilization container 800, such as, for example, the body 802. In particular, the coupling mechanism 815 on the lid 810 of one sterilization container 800 is configured to engage the recessed channel 803 on the body 802 of another sterilization container 800. In the present example, the lid 810 of the sterilization container 800 includes one coupling mechanism 815 on the exterior surface 812, however, it should be understood that in other embodiments the lid 810 may include additional coupling mechanisms 815 positioned on the exterior surface 812 and/or other surfaces of the lid 810.

The lid 810 of the sterilization container 800 further includes an inlet 816 positioned along the coupling mechanism 815, and in particular at a terminal end of the coupling mechanism 815. In some embodiments the lid 810 of the sterilization container 800 includes one or more filter structures disposed within the coupling mechanism 815 such that a tortuous path filter is formed within the coupling mechanism 815. In this instance, the inlet 816 of the lid 810 is configured to provide an ingress point into the coupling mechanism 815, and more specifically toward the tortuous filter path positioned within the coupling mechanism 815. Although not shown, it should be understood that the one or more filter structures and/or the tortuous path filter disposed within the coupling mechanism 815 of the lid 810 may be configured and operable similar to the filter structures 120, 140 shown and described above. As described in greater detail herein, the inlet 816 of the lid 810 may be positioned along various other regions of the coupling mechanism 815 and/or the exterior surface 812 without departing from the scope of the present disclosure.

Referring now to FIG. 14, a pair of sterilization containers 800 are schematically depicted in a stacked configuration with a first sterilization container 800 positioned over and received on a second sterilization container 800. In particular, the second sterilization containers 800 receives the first sterilization container 800 via a corresponding engagement between the coupling mechanism 815 of the second, lower sterilization container 800 and the recessed channel 803 of the first, upper sterilization container 800, respectively. With the recessed channel 803 sized and shaped in accordance with a size and shape of the coupling mechanism 815, the first, upper sterilization container 800 is securely coupled to the second, lower sterilization container 800 in response to the recessed channel 803 receiving the coupling mechanism 815 therein.

In particular, the plurality of engagement surfaces 805 at a juncture between the bottom wall 804 and each of the pair of end walls 808 engage the coupling mechanism 815 of the lid 810 to thereby fasten the first, upper sterilization container 800 to the second, lower sterilization container 800. The plurality of engagement surfaces 805 forming the recessed channel 803 of the body 802 are configured to inhibit a movement (e.g., lateral, longitudinal, and/or the like) of the coupling mechanism 815 of the lid 810 received therein. It should be understood that the first and second sterilization containers 800 are substantially similar and interchangeable with one another such that the description provided herein of a first and second sterilization container 800 is not intended to be limiting.

Still referring to FIG. 13, the plurality of engagement surfaces 805 of the body 802 and the coupling mechanism 815 of the lid 810 are cooperatively sized, shaped, and configured to form one or more gaps 801 between the pair of sterilization containers 800 in response to at least one sterilization container 800 being stacked atop at least another sterilization container 800. In this instance, the one or more gaps 801 extending along a longitudinal length of the sterilization containers 800 (i.e. in the +/−X direction of the coordinate axes in the figures), and more specifically between the plurality of sidewalls 806 of the body 802 on the first, upper sterilization container 800 and the exterior surface 812 of the lid 810 on the second, lower sterilization container 800. In this instance, a clearance formed by the one or more gaps 801 facilitates an ingress point to the inlet 816 of the second, lower sterilization container 800 with the first, upper sterilization container 800 disposed thereon.

IX. Alternative Stackable Sterilization Containers with Nesting Feature

Figure 15:
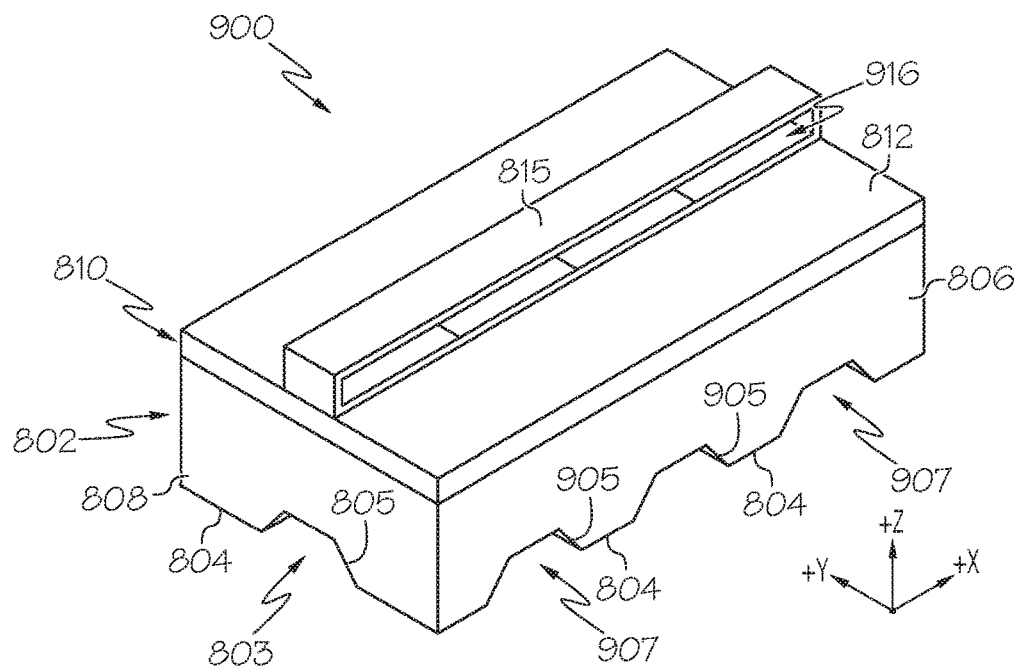
FIG. 15 is a perspective view of another exemplary sterilization container including a body, a lid, and a filter assembly having a nesting feature according to one or more embodiments shown and described herein.
Figure 16:
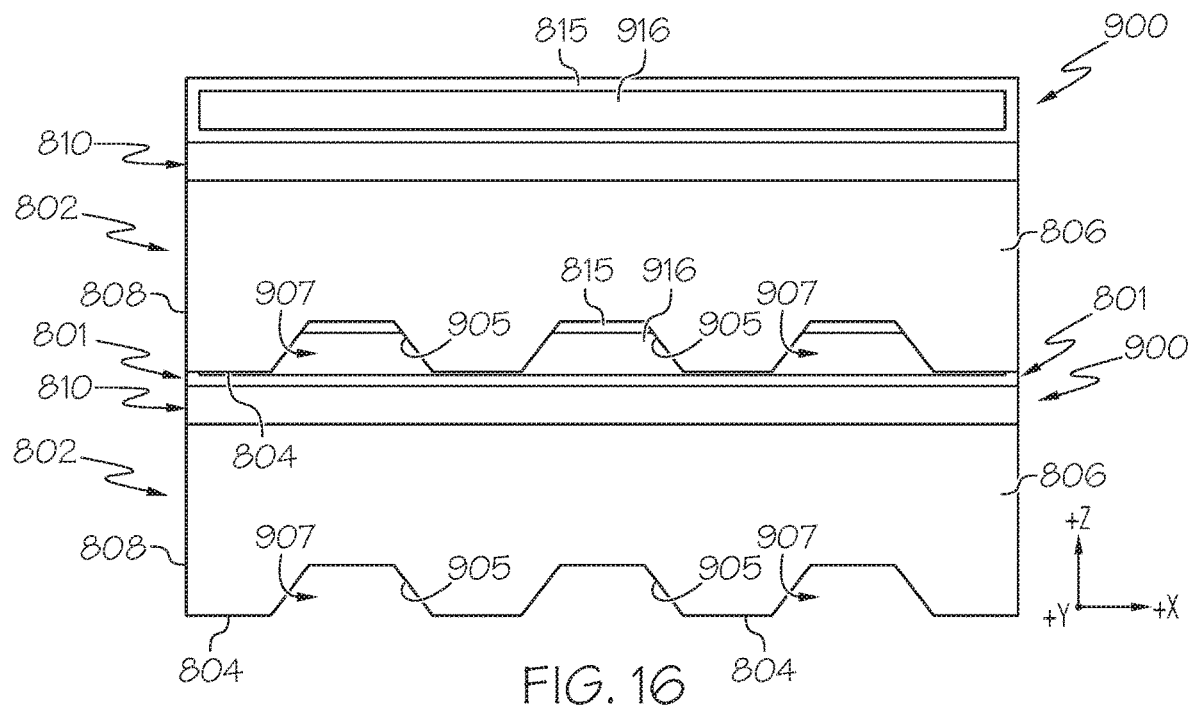
FIG. 16 is a side view of a pair of the sterilization containers of FIG. 15 stacked atop one another according to one or more embodiments shown and described herein.

FIGS. 15-16 schematically depict an alternative embodiment of a sterilization container 900 that is substantially similar to the sterilization container 800 shown and described above. Except as otherwise described below, the sterilization container 900 may be configured and operable like the sterilization container 800 such that like reference numerals are used to identify like components. For instance, referring specifically to FIG. 15, the sterilization container 900 includes the body 802 formed by the bottom wall 804, one or more sidewalls 806, and one or more end walls 808 as described above. The body 802 of the sterilization container 900 further includes one or more engagement surfaces 805 along a juncture between the bottom wall 804 and the one or more end walls 808 thereby forming one or more recessed channels 803 extending therethrough. The one or more engagement surfaces 805 positioned between the bottom wall 804 and the end walls 808 extend at varying angles, orientations, and/or configurations therethrough to form the recessed channel 803 of the body 802.

In the present example, the body 802 of the sterilization container 900 includes a pair of opposing end walls 808 defining a longitudinal length of the body 802 in the +/−X direction of FIG. 15 and a pair of opposing sidewalls 806 defining a lateral width of the body 802 in the +/−Y direction of FIG. 15. The pair of opposing end walls 808 of the body 802 includes a plurality of engagement surfaces 805 extending from the bottom wall 804 and along each of the end walls 808, thereby defining at least one recessed channel 803 thereon. In the present example, the at least one recessed channel 803 extends along a longitudinal length of the bottom wall 804 of the body 802 between the pair of end walls 808 (i.e. in the +/−X direction of the coordinate axes in the figures) and has a trapezoidal configuration. Although the body 802 of the present example depicts a single recessed channel 803 formed along the bottom wall 804, it should be understood that in other embodiments additional recessed channels 803 may be included on the body 802. As described in greater detail above, the engagement surfaces 805 are sized and shaped in accordance with a size and shape of the lid 810. It should be understood that in other embodiments the body 802 of the sterilization container 900 may include additional and/or fewer engagement surfaces 805 at a juncture between the bottom wall 804 and the end walls 808 than those shown and described herein. Additionally, in some embodiments the engagement surfaces 805 of the body 802 may include various other sizes, shapes, arrangements, and/or configurations to thereby form recessed channels with varying profiles.

Still referring to FIG. 15, the body 802 of the sterilization container 900 further includes a plurality of engagement surfaces 905 extending from the bottom wall 804 and along each of the pair of sidewalls 806, thereby defining at least one recessed channel 907 thereon. In the present example, the at least one recessed channel 907 extends along a lateral width of the bottom wall 804 of the body 802 between the pair of sidewalls 806 in the +/−Y direction of FIG. 15 and has a trapezoidal configuration. The recessed channel 803 extending through a longitudinal length of the body 802 (i.e. in the +/−X direction of the coordinate axes in the figures) intersects with and forms a connection with the plurality of recessed channels 907 extending through a lateral width of the body 802 along the bottom wall 804 (i.e. in the +/−Y direction of the coordinate axes in the figures). Although the body 802 of the present example depicts three recessed channel 907 formed along the bottom wall 804, it should be understood that in other embodiments additional recessed channels 907 may be included on the body 802. It should further be understood that in other embodiments the body 802 of the sterilization container 900 may include additional and/or fewer engagement surfaces 905 at a juncture between the bottom wall 804 and the sidewalls 906 than those shown and described herein. Additionally, in some embodiments the engagement surfaces 905 of the body 802 may include various other sizes, shapes, arrangements, and/or configurations to thereby form recessed channels with varying profiles.

The sterilization container 900 further includes the lid 810 defined by the exterior surface 812 and an opposite interior surface opposite with the at least one coupling mechanism 815 disposed on and extending outwardly from the exterior surface 812 to form a protrusion thereon. The coupling mechanism 815 of the lid 810 extends along a longitudinal length of the exterior surface 812 in the +/−X direction of FIG. 15 and is sized and shaped in accordance with a configuration of the recessed channel 803 of the body 802. Although the lid 810 of the sterilization container 900 is shown and described herein as including one coupling mechanism 815 in other embodiments the lid 810 may include additional coupling mechanisms 815 along the exterior surface 812 and/or other surfaces of the lid 810.

Still referring to FIG. 15, the lid 810 of the sterilization container 900 further includes an inlet 916 positioned along the coupling mechanism 815, and in particular along a sidewall of the coupling mechanism 815 that extends along a longitudinal length of the coupling mechanism 815. In this instance, the inlet 916 extends on the coupling mechanism 815 between the opposing end walls 808 of the lid 810. In some embodiments the lid 810 of the sterilization container 900 includes one or more filter structures disposed within the coupling mechanism 815 such that a tortuous path filter is formed therein and the inlet 916 is configured to provide an ingress point into the tortuous filter path positioned therein. Although not shown, it should be understood that the one or more filter structures and/or the tortuous path filter disposed within the coupling mechanism 815 of the lid 810 may be configured and operable similar to the filter structures 120, 140 shown and described above.

Referring now to FIG. 16, a pair of sterilization containers 900 are schematically depicted in a stacked configuration with a first sterilization container 900 positioned over and received on a second sterilization container 900. In particular, the second sterilization container 900 receives the first sterilization container 900 via a corresponding engagement between the coupling mechanism 815 of the second, lower sterilization container 900 and the recessed channel 803 of the first, upper sterilization container 900, respectively. With the recessed channel 803 sized and shaped in accordance with a size and shape of the coupling mechanism 815, the first, upper sterilization container 900 is securely coupled to the second, lower sterilization container 900 in response to the recessed channel 803 receiving the coupling mechanism 815 therein.

In particular, the plurality of engagement surfaces 805 at a juncture between the bottom wall 804 and each of the pair of end walls 808 engage the coupling mechanism 815 of the lid 810 to thereby fasten the first, upper sterilization container 900 to the second, lower sterilization container 900. The plurality of engagement surfaces 805 forming the recessed channel 803 of the body 802 are configured to inhibit a movement (e.g., lateral, longitudinal, and/or the like) of the coupling mechanism 815 of the lid 810 received therein. It should be understood that the first and second sterilization containers 900 are substantially similar and interchangeable with one another such that the description provided herein of a first and second sterilization container 900 is not intended to be limiting.

Still referring to FIG. 16, the plurality of engagement surfaces 805 of the body 802 and the coupling mechanism 815 of the lid 810 are cooperatively sized, shaped, and configured to form one or more gaps 801 between the pair of sterilization containers 900 in response to at least one sterilization container 900 being stacked atop at least another sterilization container 900. In this instance, the one or more gaps 801 extend along a longitudinal length of the sterilization containers 900 in the +/−X direction of FIG. 16, and more specifically between the pair of sidewalls 806 of the body 802 on the first, upper sterilization container 900 and the exterior surface 812 of the lid 810 on the second, lower sterilization container 900. In this instance, a clearance formed by the one or more gaps 801 facilitates an ingress point to the inlet 916 of the second, lower sterilization container 900 with the first, upper sterilization container 900 disposed thereon.

Additionally, the plurality of recessed channels 907 included along the pair of sidewalls 806 of the first, upper sterilization container 900 facilitates a plurality of ingress points to the inlet 916 of the second, lower sterilization container 900 with the first, upper sterilization container 900 disposed thereon. With the inlet 916 included on a sidewall of the coupling mechanism 815 of the second, lower sterilization container 900, access thereto is provided via the plurality of recessed channels 907 included on the pair of sidewalls 806 of the body 802 of the first, upper sterilization container 900. In this instance, the plurality of recessed channels 907 of the upper sterilization container 900 are configured to align with the inlet 916 of the lower sterilization container 900 in response to the coupling mechanism 815 of the lower sterilization container 900 receiving and/or engaging the recessed channel 803 of the upper sterilization container 900.

X. Alternative Sterilization Container with Rectangular Tortuous Path Filter

Figure 17:
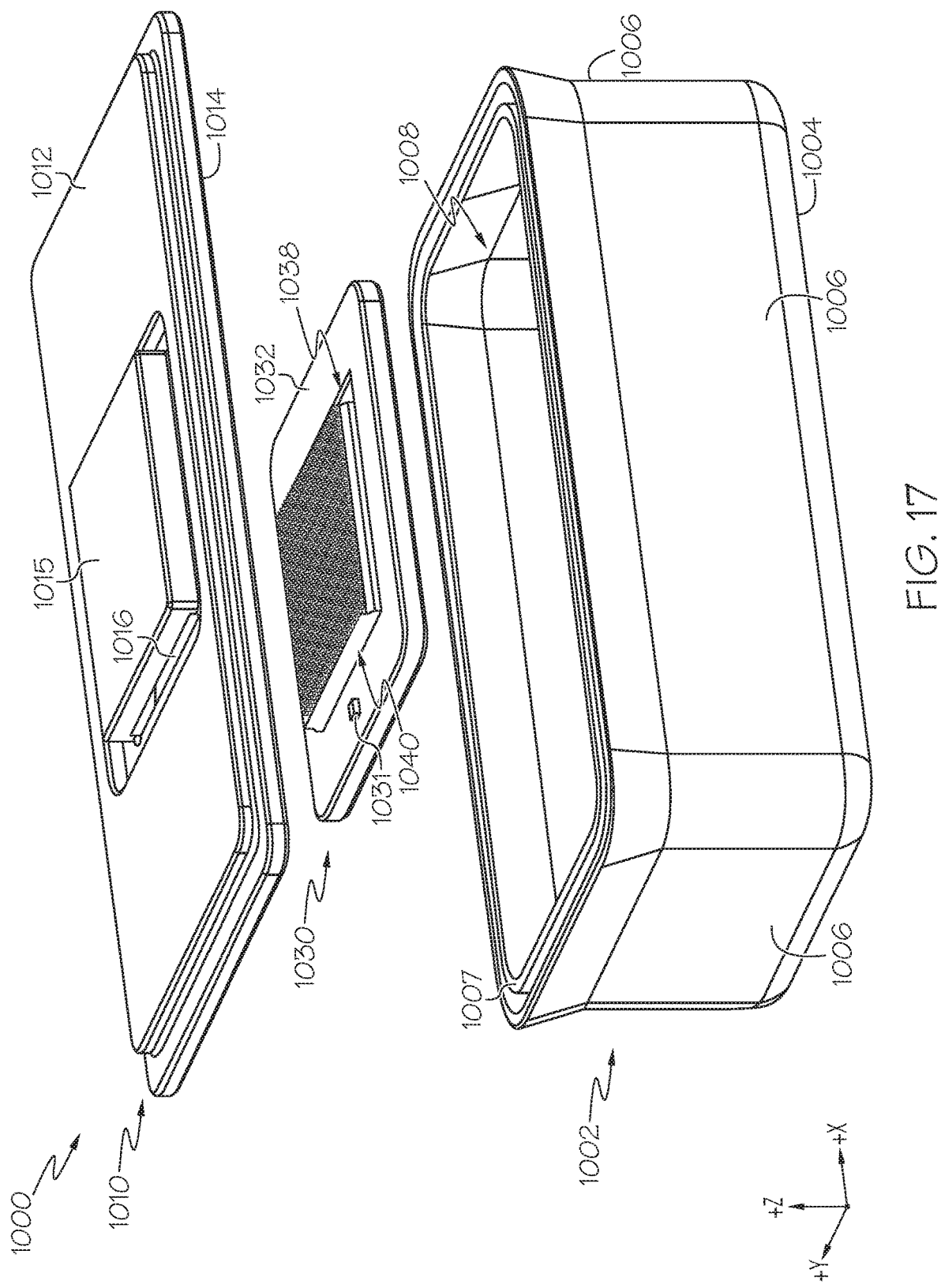
FIG. 17 is an exploded perspective view of another exemplary sterilization container including a body, a lid, and a filter assembly according to one or more embodiments shown and described herein.
Figure 18:
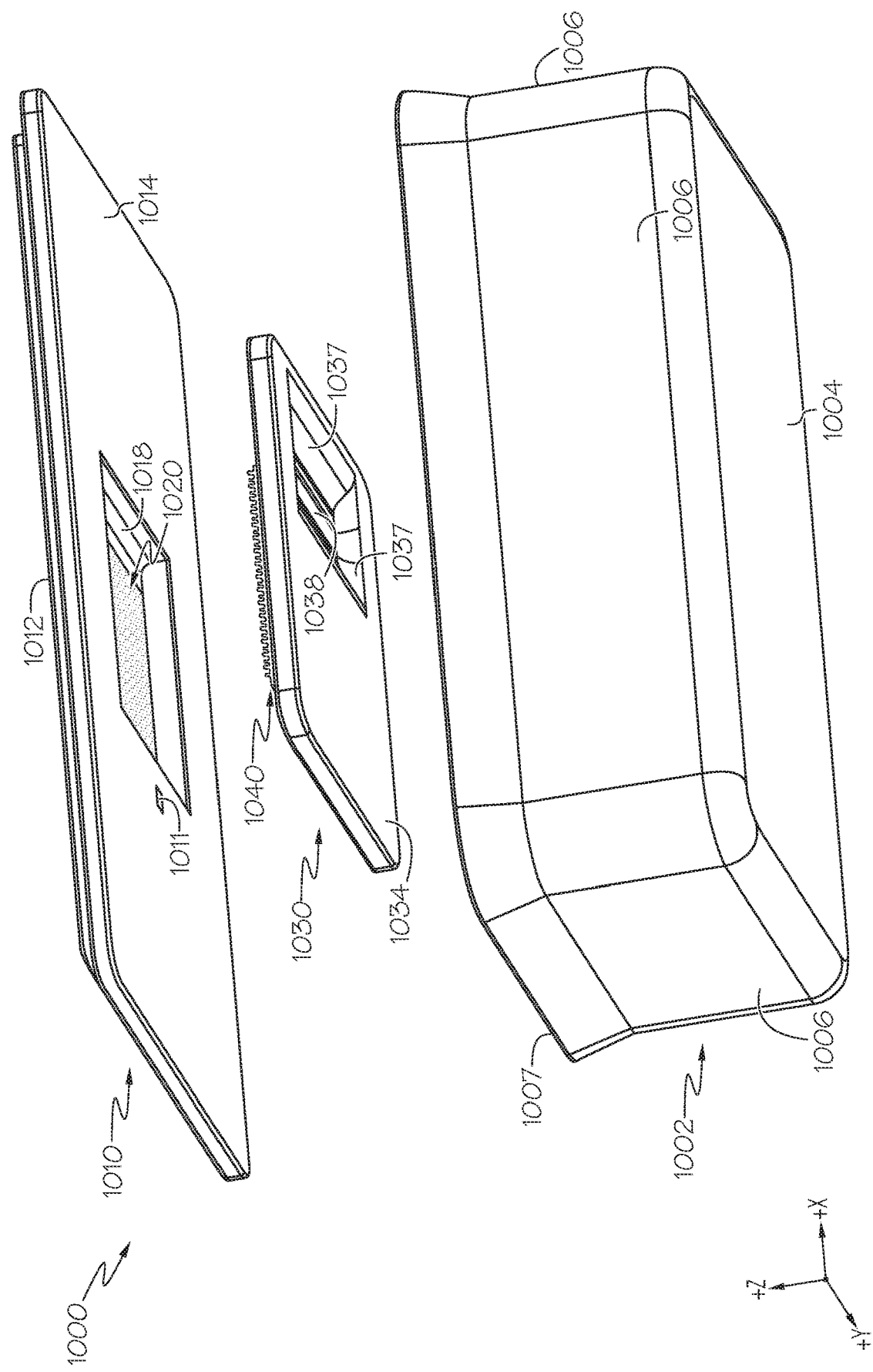
FIG. 18 is an exploded perspective view of the sterilization container of FIG. 17 according to one or more embodiments shown and described herein.
Figure 19:
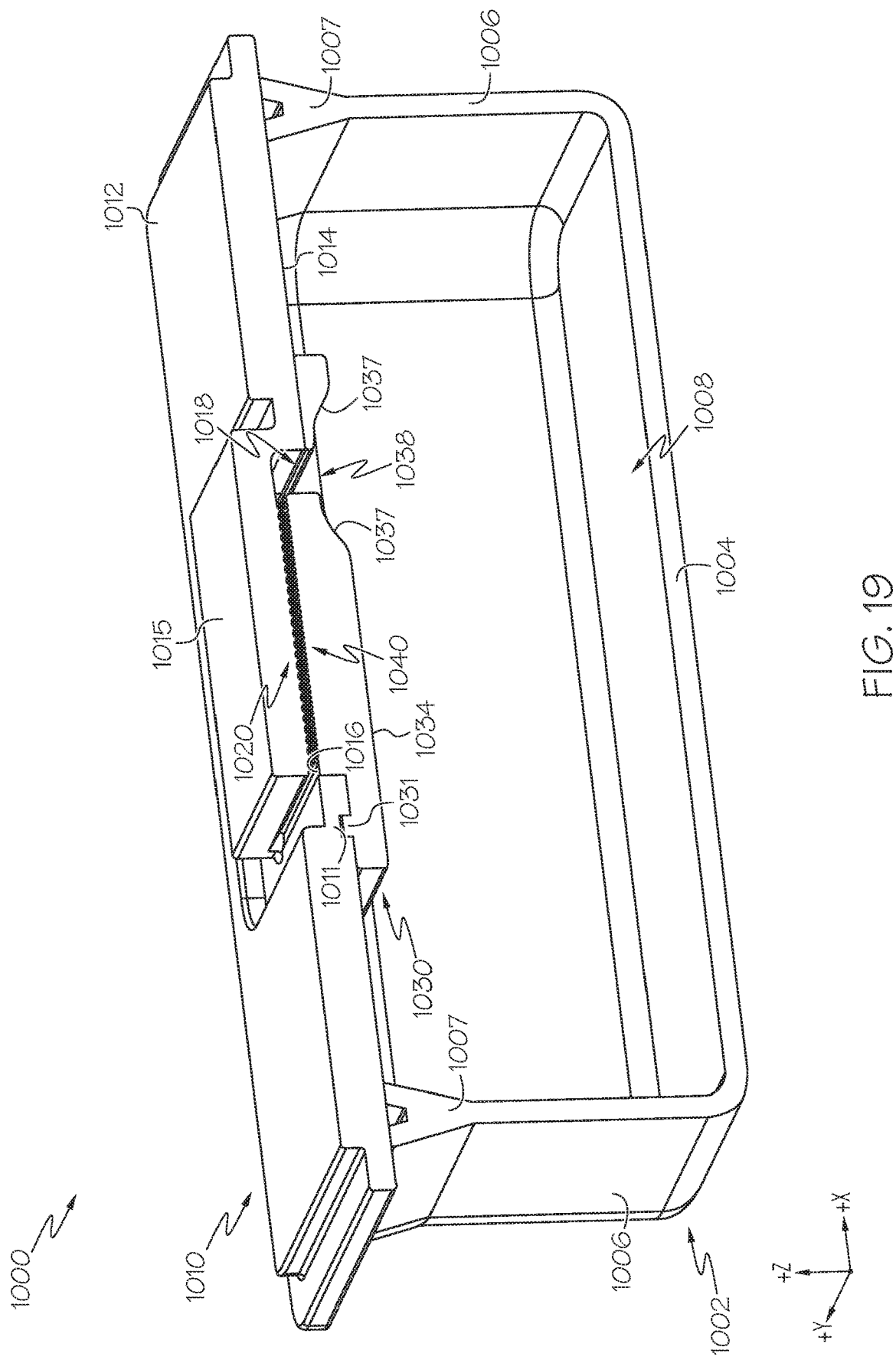
FIG. 19 is a cross-sectional view of the sterilization container of FIG. 17 with the lid coupled to the filter assembly and forming a tortuous filter path according to one or more embodiments shown and described herein.

Referring now to FIGS. 17-19, an alternative embodiment of a sterilization container 1000 that is substantially similar to the sterilization container 100, 200, 300 shown and described above is schematically depicted. Except as otherwise described below, the sterilization container 1000 may be configured and operable like the sterilization containers 100, 200, 300. For instance, the sterilization container 1000 includes a body 1002 formed by a bottom wall 1004, a plurality of sidewalls 1006, and an open, top end 1007 that collectively define an interior volume 1008 therein. The interior volume 1008 of the body 1002 is generally sized to receive one or more devices therein, such as, for example, medical apparatuses, instruments, and/or the like. The sterilization container 1000 includes a lid 1010 that is secured to the body 1002 and includes an exterior surface 1012 and an interior surface 1014 opposite of the exterior surface 1012. In particular, the interior surface 1014 of the lid 1010 is configured to engage the open, top end 1007 of the body 102. The exterior surface 1012 of the lid 1010 includes a filter structure housing 1015 and a recessed inlet 1016 disposed thereon. As described in greater detail herein, the filter structure housing 1015 is sized and shaped to receive one or more components of the sterilization container 1000 therein, such as, for example, a filter assembly 1030.

The sterilization container 1000 further includes the filter assembly 1030 having an exterior surface 1032 and an interior surface 1034 positioned opposite of the exterior surface 1032. The exterior surface 1032 of the filter assembly 1030 includes an exterior filter structure 1040 disposed thereon that is sized and shaped in accordance with the filter structure housing 1015 of the lid 1010, such that the exterior filter structure 1040 is configured to be received within the filter structure housing 1015 when the filter assembly 1030 is coupled to the lid 1010. Except as otherwise described below, it should be understood that the exterior filter structure 1040 of the filter assembly 1030 is substantially similar and configured like the interior filter structure 140 of the filter assembly 130 shown and described above. For instance, the exterior filter structure 1040 of the filter assembly 1030 includes a plurality of ridges and troughs disposed thereon similar to the plurality of ridges 142 and troughs 144 of the interior filter structure 140. However, the exterior filter structure 1040 is formed along the exterior surface 1032 of the filter assembly 1030, rather than the interior surface 1034 as shown and described above with respect to the interior filter structure 140 of the filter assembly 130.

Still referring to FIG. 17, the exterior surface 1032 of the filter assembly 1030 further includes one or more latch elements 1031 disposed thereon. The one or more latch elements 1031 of the filter assembly 1030 are sized, shaped and configured to securely couple the filter assembly 1030 to the lid 1010 by engaging one or more corresponding features of the lid 1010, such as, for example, one or more latch elements 1011 positioned along the interior surface 1014 (see FIG. 18). It should be understood that the one or more latch elements 1031 of the filter assembly 1030 are configured substantially similar to the one or more latch elements 131 of the filter assembly 130 shown and described above.

Referring now to FIG. 18, the interior surface 1014 of the lid 1010 is depicted including the one or more latch elements 1011 disposed thereon. As similarly described in greater detail above with respect to the lid 110 of the sterilization container 100, the one or more latch elements 1011 are sized, shaped and configured to securely couple the lid 1010 to one or the filter assembly 1030 of the sterilization container 1000. The interior surface 1014 of the lid 1010 further includes an interior filter structure 1020 disposed thereon, wherein the interior filter structure 1020 extends along the interior surface 1014 and is positioned between the recessed inlet 1016 and an outlet opening 1018 of the lid 1010. Except as otherwise described below, it should be understood that the interior filter structure 1020 of the lid 1010 is substantially similar and configured like the exterior filter structure 120 of the lid 110 shown and described above. For instance, the interior filter structure 1020 of the lid 1010 includes a plurality of ridges and troughs disposed thereon similar to the plurality of ridges 122 and troughs 124 of the exterior filter structure 120. However, the interior filter structure 1020 is formed along the interior surface 1014 of the lid 1010, rather than the exterior surface 1012 as shown and described above with respect to the exterior filter structure 120 of the lid 110.

The filter assembly 1030 of the sterilization container 1000 further includes one or more ramps 1037 positioned along the interior surface 1034. In particular, the one or more ramps 1037 are disposed about the outlet opening 1038 of the filter assembly 1030, with a longitudinal length of the one or more ramps 1037 extending parallel to a width of the outlet opening 1038. The one or more ramps 1037 forms a sloped-surface from the interior surface 1034 of the filter assembly 1030 toward the outlet opening 1038. The outlet opening 1038 of the filter assembly 1030 is positioned adjacent to a terminal end of the exterior filter structure 1040. In the present example, the exterior filter structure 1040 of the filter assembly 1030 is integrally-formed with the exterior surface 1032 such that the exterior filter structure 1040 forms a unitary structure with the filter assembly 1030.

Still referring to FIG. 18, the interior filter structure 1020 of the lid 1010 is integrally-formed with the interior surface 1014 such that the interior filter structure 1020 forms a unitary structure with the lid 1010. However, it should be understood that in other embodiments one or more of the filter structures 1020, 1040 may be removably assembled to the lid 1010 such that the interior filter structure 1020 is not integrally-formed with the lid 1010. In this instance, the interior filter structure 1020 and the exterior filter structure 1040 may be preassembled to one another and configured to be selectively assembled onto the lid 1010. It should be understood that in other embodiments one or more filter structures may be integrally formed and/or removably assembled onto the bottom wall 1004 of the body 1002 without departing from a scope of the present disclosure. In this instance, the sterilization container 1000 may include the interior filter structure 1020 along the lid 1010, the exterior filter structure 1040 along the filter assembly 1030, and an additional filter structure along the bottom wall 1004 of the body 1002 to facilitate an ingress and egress through the interior volume 1008.

Referring now to FIG. 19, the interior surface 1014 of the lid 1010 is coupled to the plurality of sidewalls 1006 of the body 1002 by engaging the open, top end 1007. The exterior surface 1032 of the filter assembly 1030 is secured to the interior surface 1014 of the lid 1010 via a corresponding engagement of the one or more latch elements 1011, 1031. In this instance, the filter assembly 1030 is disposed within the interior volume 1008 of the body 1002 with the exterior filter structure 1040 of the filter assembly 1030 positioned relatively beneath the interior filter structure 1020 of the lid 1010. More specifically, the exterior filter structure 1040 of the filter assembly 1030 is received within the filter structure housing 1015 of the lid 1010 such that the exterior filter structure 1040 meshes with the interior filter structure 1020, thereby forming a rectangular tortuous filter path therebetween. The outlet opening 1018 of the lid 1010 is coupled to, and aligned with, the outlet opening 1038 of the filter assembly 1030 when the filter assembly 1030 is received within and coupled to the lid 1010 of the sterilization container 1000.

Securing the exterior surface 1032 of the filter assembly 1030 onto the interior surface 1014 of the lid 1010 via the engagement of the corresponding latch elements 1011 of the lid 1010 and the latch element 1031 of the filter assembly 1030, respectively, provides a coupling of the interior filter structure 1020 of the lid 1010 with the exterior filter structure 1040 of the filter assembly 1030. In this instance, a tortuous path filter is formed between the lid 1010 and the filter assembly 1030 within the interior volume 1008 of the body 1002. In particular, a rectangular tortuous path filter is formed due a rectangularly-shaped profile of the interior filter structure 1020 of the lid 1010 and a rectangularly-shaped profile of the exterior filter structure 1040 of the filter assembly 1030. The sterilization container 1000 includes an ingress point into the tortuous path filter formed by the interior filter structure 1020 of the lid 1010 and the exterior filter structure 1040 of the filter assembly 1030 at the recessed inlet 1016. Additionally, the sterilization container 1000 includes a single egress point from the tortuous path filter via the outlet opening 1018 of the lid 1010 and the outlet opening 1038 of the filter assembly 1030 aligned therewith, respectively.

Further aspects are provided by the subject matter in the following clauses:

1. A sterilization container for sterilizing medical instruments, the sterilization container comprising: a body defining an interior volume; a lid connected to the body and configured to seal the interior volume between the lid and the body, the lid comprising an exterior filter structure integrally formed thereon, the exterior filter structure comprising: a first plurality of ridges; and a first plurality of troughs formed between the first plurality of ridges; a filter assembly connected to the lid and comprising an interior filter structure integrally formed thereon, the interior filter structure comprising: a second plurality of ridges; and a second plurality of troughs formed between the second plurality of ridges; wherein the first plurality of ridges of the exterior filter structure are interposed between the second plurality of ridges of the interior filter structure; and wherein the exterior filter structure and the interior filter structure are configured to form a series of longitudinal channels positioned between the lid and the filter assembly to define a rectangular tortuous filter path that inhibits ingress and egress from the interior volume.

2. The sterilization container of any preceding clause, wherein at least one trough of the second plurality of troughs has a length that extends at least two ridges of the first plurality of ridges.

3. A sterilization container comprising: a body defining an interior volume; a lid coupled to the body and configured to seal the interior volume therebetween, the lid includes a first filter structure comprising: a first plurality of ridges; and a first plurality of troughs formed between the first plurality of ridges; a filter assembly coupled to the lid and configured to seal the first filter structure therebetween, the filter assembly includes a second filter structure comprising: a second plurality of ridges; and a second plurality of troughs formed between the second plurality of ridges; wherein the first filter structure is configured to mesh with the second filter structure such that the first plurality of ridges is coupled to the second plurality of troughs and the first plurality of troughs is coupled to the second plurality of ridges; and wherein the first filter structure and the second filter structure are configured to form a series of longitudinal channels positioned between the lid and the filter assembly to define a rectangular tortuous filter path that inhibits ingress and egress from the interior volume.

4. The sterilization container of any preceding clause, wherein the lid includes a first inlet opening and a first outlet opening disposed about opposing ends of the first filter structure, and the filter assembly includes a second inlet opening and a second outlet opening disposed about opposing ends of the second filter structure.

5. The sterilization container of any preceding clause, wherein the first inlet opening is in communication with the second inlet opening and the first outlet opening is in communication with the second outlet opening in response to the first filter structure meshing with the second filter structure.

6. The sterilization container of any preceding clause, wherein the first inlet opening is a recessed depression along an exterior surface of the lid, and the second inlet opening is an aperture extending through the filter assembly.

7. The sterilization container of any preceding clause, wherein the filter assembly includes one or more ramps disposed about the second inlet opening that define curved surfaces extending from an exterior surface of the filter assembly toward the second inlet opening.

8. The sterilization container of any preceding clause, wherein the one or more ramps are configured to direct airflow toward the second inlet opening of the filter assembly.

9. The sterilization container of any preceding clause, wherein the lid includes a plurality of first filter structures disposed along an exterior surface of the lid and the filter assembly includes a plurality of second filter structures disposed along an interior surface of the filter assembly.

10. The sterilization container of any preceding clause, wherein the body is sized and shaped to receive one or more medical devices within the interior volume.

11. A modular lid of a sterilization container comprising: a modular body including an inlet and a plurality of movable body segments, wherein the modular body is configured to selectively expand and collapse the plurality of movable body segments relative to one another to thereby selectively adjust a longitudinal length of the modular lid; a first filter structure disposed within the modular body and including a first plurality of ridges and a first plurality of troughs formed between the first plurality of ridges; and a second filter structure disposed within the modular body and including a second plurality of ridges and a second plurality of troughs formed between the second plurality of ridges; wherein the first filter structure is to the second filter structure such that the first plurality of ridges is coupled to the second plurality of troughs and the first plurality of troughs is coupled to the second plurality of ridges thereby forming a series of rectangular channels within the modular body to define a rectangular tortuous filter path that inhibits ingress and egress from the sterilization container; and wherein the first filter structure and the second filter structure are configured to expand and collapse in response to expansion and collapse of the plurality of movable body segments of the modular body.

12. The modular lid of any preceding clause, wherein the first filter structure is configured to expand the first plurality of ridges and the first plurality of troughs in response to an expansion of the modular body, and further configured to collapse the first plurality of ridges and the first plurality of troughs in response to a collapse of the modular body.

13. The modular lid of any preceding clause wherein the second filter structure is configured to expand the second plurality of ridges and the second plurality of troughs in response to an expansion of the modular body, and further configured to collapse the second plurality of ridges and the second plurality of troughs in response to a collapse of the modular body.

14. The modular lid of any preceding clause, wherein expanding the first plurality of ridges and the first plurality of troughs includes forming additional ridges and troughs within the first filter structure.

15. The modular lid of any preceding clause, wherein expanding the second plurality of ridges and the second plurality of troughs includes forming additional ridges and troughs within the second filter structure.

16. The modular lid of any preceding clause, wherein the inlet is configured to expand in response to an expansion of the modular body, and further configured to collapse in response to a collapse of the modular body.

17. The modular lid of any preceding clause, wherein the inlet is configured to maintain a fixed configuration in response to an expansion and collapse of the modular body.

18. A sterilization container comprising: a body including a bottom wall and a plurality of sidewalls extending outwardly therefrom to define an interior volume disposed therebetween, each of the plurality of sidewalls includes a first filter structure comprising: a first plurality of ridges; and a first plurality of troughs formed between the first plurality of ridges; a lid coupled to the body and configured to seal the interior volume therein, the lid including a top wall and a plurality of sidewalls extending outwardly therefrom, each of the plurality of sidewalls includes a second filter structure comprising: a second plurality of ridges; and a second plurality of troughs formed between the second plurality of ridges; wherein the plurality of sidewalls of the lid are received within the interior volume and positioned against the plurality of sidewalls of the body such that the first filter structures along the first plurality of sidewalls are configured to mesh with the second filter structures along the second plurality of sidewalls of the lid; and wherein the first filter structures and the second filter structures are configured to form a series of rectangular channels positioned between the lid and the body to define a rectangular tortuous filter path that inhibits ingress and egress from the interior volume.

19. The sterilization container of any preceding clause, wherein the first plurality of ridges of the first filter structures positioned along the first plurality of sidewalls are coupled to the second plurality of troughs of the second filter structures positioned along the second plurality of sidewalls.

20. The sterilization container of any preceding clause, wherein the first plurality of troughs of the first filter structures positioned along the first plurality of sidewalls are coupled to the second plurality of ridges of the second filter structures positioned along the second plurality of sidewalls.

21. The sterilization container of any preceding clause, wherein the lid is configured to form a plurality of inlets between the top wall, the plurality of sidewalls of the lid, and the plurality of sidewalls of the body in response to the lid coupling the base.

22. The sterilization container of any preceding clause, wherein the lid is configured to form a plurality of outlet openings between the bottom wall, the plurality of sidewalls of the lid, and the plurality of sidewalls of the body in response to the lid coupling the base.

23. The sterilization container of any preceding clause, wherein the bottom wall of the body includes one or more standoffs extending outwardly therefrom adjacent to the plurality of sidewalls, wherein the one or more standoffs at least partially define the plurality of outlet openings.

24. The sterilization container of any preceding clause, wherein the plurality of sidewalls of the lid includes one or more standoffs extending outwardly therefrom opposite of the top wall, wherein the one or more standoffs at least partially define the plurality of outlet openings.

25. A sterilization container comprising: a body defining an interior volume; a lid coupled to the body and configured to seal the interior volume therebetween, the lid includes a first radial filter structure comprising: a first plurality of dimples; and a first plurality of ledges formed about the first plurality of dimples; a filter assembly coupled to the lid and configured to seal the first radial filter structure therebetween, the filter assembly includes a second radial filter structure comprising: a second plurality of dimples; and a second plurality of ledges formed about the second plurality of dimples; wherein the first radial filter structure is configured to mesh with the second radial filter structure such that the first plurality of dimples is coupled to the second plurality of dimples and the first plurality of ledges is coupled to the second plurality of ledges; and wherein the first radial filter structure and the second radial filter structure are configured to form a series of recessed depressions positioned between the lid and the filter assembly to define a radial tortuous filter path that inhibits ingress and egress from the interior volume.

26. The sterilization container of any preceding clause, wherein the lid includes a first inlet opening disposed at a center of the first radial filter structure and a plurality of first outlet openings disposed about a boundary of the first radial filter structure.

27. The sterilization container of any preceding clause, wherein the filter assembly includes a second inlet opening disposed at a center of the second radial filter structure and a second outlet opening disposed about a boundary of the second radial filter structure.

28. The sterilization container of any preceding clause, wherein the first inlet opening is in communication with the second inlet opening and the plurality of first outlet openings are in communication with the second outlet opening in response to the first radial filter structure meshing with the second radial filter structure.

29. The sterilization container of any preceding clause, wherein the first inlet opening is a recessed depression along an exterior surface of the lid, and the second inlet opening is an aperture extending through the filter assembly.

30. The sterilization container of any preceding clause, wherein the filter assembly includes one or more ramps disposed about the second inlet opening that define curved surfaces extending from an exterior surface of the filter assembly toward the second inlet opening.

31. The sterilization container of any preceding clause, wherein the one or more ramps are configured to direct airflow toward the second inlet opening of the filter assembly.

32. The sterilization container of any preceding clause, wherein the body is sized and shaped to receive one or more medical devices within the interior volume.

33. A stackable sterilization container comprising: a body including a bottom wall and a plurality of sidewalls extending outwardly therefrom to define an interior volume disposed therebetween, wherein the bottom wall includes one or more recessed channels extending between the plurality of sidewalls; and a lid coupled to the body and configured to seal the interior volume therein, the lid including: a top wall; and an engagement mechanism extending outwardly from the top wall, the engagement mechanism includes an inlet and one or more filter structures disposed therein, the engagement mechanism is sized and shaped relative to the one or more recessed channels such that the engagement mechanism is configured to engage the recessed channel; wherein the one or more filter structures are configured to form a series of rectangular channels within the lid to define a rectangular tortuous filter path that inhibits ingress and egress from the interior volume; wherein the one or more recessed channels are configured to form gaps to access the inlet of the lid when the engagement mechanism is received within at least one of the one or more recessed channels.

34. A sterilization container for sterilizing medical instruments, the sterilization container comprising: a body defining an interior volume; a lid connected to the body and configured to seal the interior volume between the lid and the body, the lid comprising an interior filter structure positioned thereon, the interior filter structure comprising: a first plurality of ridges; and a first plurality of troughs formed between the first plurality of ridges; a filter assembly connected to the lid and comprising an exterior filter structure positioned thereon, the interior filter structure comprising: a second plurality of ridges; and a second plurality of troughs formed between the second plurality of ridges; wherein the first plurality of ridges of the exterior filter structure are interposed between the second plurality of ridges of the interior filter structure; and wherein the interior filter structure and the exterior filter structure are configured to form a series of longitudinal channels positioned between the lid and the filter assembly to define a rectangular tortuous filter path that inhibits ingress and egress from the interior volume.

35. The sterilization container of any preceding clause, wherein the interior filter structure is integrally-formed on the lid such that the interior filter structure and the lid are a unitary structure.

36. The sterilization container of any preceding clause, wherein the interior filter structure is releasably coupled to the lid such that the interior filter structure is configured to selectively engage the lid.

37. The sterilization container of any preceding clause, wherein the exterior filter structure is integrally-formed on the filter assembly such that the exterior filter structure and the filter assembly are a unitary structure.

38. The sterilization container of any preceding clause, wherein the exterior filter structure is releasably coupled to the filter assembly such that the exterior filter structure is configured to selectively engage the filter assembly.

39. A sterilization container comprising: a body defining an interior volume; a lid coupled to the body and configured to seal the interior volume therebetween, the lid includes a first filter structure disposed within the interior volume and comprising: a first plurality of ridges; and a first plurality of troughs formed between the first plurality of ridges; a filter assembly coupled to the lid and disposed within the interior volume, the filter assembly is configured to seal the first filter structure therebetween and includes a second filter structure comprising: a second plurality of ridges; and a second plurality of troughs formed between the second plurality of ridges; wherein the first filter structure is configured to mesh with the second filter structure such that the first plurality of ridges is coupled to the second plurality of troughs and the first plurality of troughs is coupled to the second plurality of ridges; and wherein the first filter structure and the second filter structure are configured to form a series of longitudinal channels positioned between the lid and the filter assembly to define a rectangular tortuous filter path that inhibits ingress and egress from the interior volume.

40. A sterilization container comprising: a body defining an interior volume; a lid coupled to the body and configured to seal the interior volume therebetween, a filter assembly releasably coupled to the lid, the filter assembly comprising a first filter structure coupled to a second filter structure, wherein the first filter structure includes a first plurality of ridges and a first plurality of troughs formed between the first plurality of ridges, and the second filter structure includes a second plurality of ridges and a second plurality of troughs formed between the second plurality of ridges; wherein the first plurality of ridges mesh with the second plurality of troughs and the first plurality of troughs mesh with the second plurality of ridges, thereby forming a series of longitudinal channels positioned therebetween and defining a rectangular tortuous filter path that inhibits ingress and egress through the filter assembly.

41. The sterilization container of any preceding clause, wherein the filter assembly is configured to selectively engage the lid such that the rectangular tortuous filter path is removable from the lid.

42. The sterilization container of any preceding clause, wherein the filter assembly is coupled to the lid along an exterior surface of the lid such that the filter assembly is external of the interior volume of the body.

43. The sterilization container of any preceding clause, wherein the filter assembly is coupled to the lid along an interior surface of the lid such that the filter assembly is disposed within the interior volume of the body.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

For the purposes of describing and defining the present invention it is noted that the term "substantially" is used herein to represent the inherent degree of uncertainty that may be attributed to any quantitative comparison, value, measurement, or other representation. The term "substantially" is used herein also to represent the degree by which a quantitative representation may vary from a stated reference without resulting in a change in the basic function of the subject matter at issue. As such, it is used to represent the inherent degree of uncertainty that may be attributed to any quantitative comparison, value, measurement, or other representation, referring to an arrangement of elements or features that, while in theory would be expected to exhibit exact correspondence or behavior, may in practice embody something slightly less than exact.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A sterilization container comprising:
   a body defining an interior volume;
   a lid coupled to the body and configured to seal the interior volume therebetween, the lid includes a first filter structure comprising:
      a first plurality of ridges; and
      a first plurality of troughs formed between the first plurality of ridges;
   a filter assembly coupled to the lid and configured to seal the first filter structure therebetween, the filter assembly includes a second filter structure comprising:
   a second plurality of ridges; and
      a second plurality of troughs formed between the second plurality of ridges;
   wherein the first filter structure is configured to mesh with the second filter structure such that the first plurality of ridges is coupled to the second plurality of troughs and the first plurality of troughs is coupled to the second plurality of ridges; and
   wherein the first filter structure and the second filter structure are configured to form a series of longitudinal channels positioned between the lid and the filter assembly to define a rectangular tortuous filter path that inhibits ingress and egress from the interior volume;
   wherein the lid includes a first inlet opening and a first outlet opening disposed at opposing ends of the first filter structure.

2. The sterilization container of claim 1, wherein the filter assembly includes a second inlet opening and a second outlet opening disposed at opposing ends of the second filter structure.

3. The sterilization container of claim 2, wherein the first inlet opening is in communication with the second inlet opening and the first outlet opening is in communication with the second outlet opening in response to the first filter structure meshing with the second filter structure.

4. The sterilization container of claim 3, wherein the first inlet opening is a recessed depression along an exterior surface of the lid, and the second inlet opening is an aperture extending through the filter assembly.

5. The sterilization container of claim 4, wherein the filter assembly includes one or more ramps disposed about the second inlet opening that define curved surfaces extending from an exterior surface of the filter assembly toward the second inlet opening.

6. The sterilization container of claim 5, wherein the one or more ramps are configured to direct airflow toward the second inlet opening of the filter assembly.

7. The sterilization container of claim 1, wherein the lid includes a plurality of first filter structures disposed along an exterior surface of the lid and the filter assembly includes a plurality of second filter structures disposed along an interior surface of the filter assembly.

8. The sterilization container of claim 1, wherein the body is sized and shaped to receive one or more medical devices within the interior volume.

9. The sterilization container of claim 1, wherein the body includes a body inlet and a plurality of movable body segments, wherein the body is configured to selectively expand and collapse the plurality of movable body segments relative to one another to thereby selectively adjust a longitudinal length of the lid;

wherein the first filter structure and the second filter structure are configured to expand and collapse in response to expansion and collapse of the plurality of movable body segments of the body.

10. The sterilization container of claim 9, wherein the first filter structure is configured to expand the first plurality of ridges and the first plurality of troughs in response to an expansion of the body, and further configured to collapse the first plurality of ridges and the first plurality of troughs in response to a collapse of the body.

11. The sterilization container of claim 9, wherein the second filter structure is configured to expand the second plurality of ridges and the second plurality of troughs in response to an expansion of the body, and further configured to collapse the second plurality of ridges and the second plurality of troughs in response to a collapse of the body.

12. The sterilization container of claim 11, wherein expanding the first plurality of ridges and the first plurality of troughs includes forming additional ridges and troughs within the first filter structure.

13. The sterilization container of claim 11, wherein expanding the second plurality of ridges and the second plurality of troughs includes forming additional ridges and troughs within the second filter structure.

14. The sterilization container of claim 9, wherein the inlet is configured to expand in response to an expansion of the modular body, and further configured to collapse in response to a collapse of the modular body.

15. The sterilization container of claim 9, wherein the inlet is configured to maintain a fixed configuration in response to an expansion and collapse of the modular body.

\* \* \* \* \*